United States Patent
Henrich et al.

(10) Patent No.: US 6,828,462 B2
(45) Date of Patent: Dec. 7, 2004

(54) UNSATURATED 1-AMINO-ALKYLCYCLOHEXANE NMDA, 5HT$_3$, AND NEURONAL NICOTINIC RECEPTOR ANTAGONISTS

(75) Inventors: Markus Henrich, Wetzlar (DE); Wojciech Danysz, Nidderau (DE); Christopher Graham Raphael Parsons, Nidderau (DE); Ivars Kalvinsh, Salaspils (LV); Valerjans Kauss, Riga (LV); Aigars Jirgensons, Riga (LV); Markus Gold, Nauheim (DE)

(73) Assignee: Merz Pharma GmbH & Co. KGAA, Frankfurt Main (DE)

( * ) Notice: Subject to any disclaimer, the term of this patent is extended or adjusted under 35 U.S.C. 154(b) by 0 days.

(21) Appl. No.: 10/288,819

(22) Filed: Nov. 6, 2002

(65) Prior Publication Data

US 2003/0166634 A1 Sep. 4, 2003

Related U.S. Application Data

(60) Provisional application No. 60/337,858, filed on Nov. 8, 2001, and provisional application No. 60/350,974, filed on Nov. 7, 2001.

(51) Int. Cl.$^7$ .................. A61K 31/33; A61K 31/55; A61K 31/445; A61K 31/40; C07C 203/04
(52) U.S. Cl. .................. 564/462; 564/453; 564/454; 564/455; 546/192; 514/317; 514/579; 514/659
(58) Field of Search ................. 564/453–455, 564/462; 546/192; 514/317, 579, 659

(56) References Cited

U.S. PATENT DOCUMENTS

| | | | | |
|---|---|---|---|---|
| 4,267,366 A | * | 5/1981 | Kane et al. | 560/231 |
| 6,034,134 A | * | 3/2000 | Gold et al. | 514/579 |
| 6,071,966 A | | 6/2000 | Gold et al. | |

* cited by examiner

*Primary Examiner*—Brian J. Davis
(74) *Attorney, Agent, or Firm*—The Firm of Hueschen and Sage

(57) ABSTRACT

Unsaturated 1-Amino-alkylcyclohexane compounds which are systemically-active as NMDA, 5HT$_3$, and nicotinic receptor antagonists, pharmaceutical compositions comprising the same, method of preparation thereof, and method of treating CNS disorders which involve disturbances of glutamatergic, serotoninergic, and nicotinic transmission, treating immunomodulatory disorders, and antimalaria, antitrypanosomal, anti-Borna virus, anti-HSV and anti-Hepatitis C virus activity.

9 Claims, 3 Drawing Sheets

UNSATURATED 1-AMINO-ALKYLCYCLOHEXANE NMDA, 5HT$_3$, AND NEURONAL NICOTINIC RECEPTOR ANTAGONISTS

BACKGROUND OF THE INVENTION

1. Field of the Invention

Unsaturated 1-Amino-alkylcyclohexane compounds which are systemically-active as NMDA, 5HT$_3$, and nicotinic receptor antagonists, pharmaceutical compositions comprising the same, method of preparation thereof, and method of treating CNS disorders which involve disturbances of glutamatergic, serotoninergic, and nicotinic transmission therewith, for treating immunomodulatory disorders, and for treating infectious diseases.

2. Prior Art

NMDA Antagonists

Antagonism of glutamate receptors of the N-methyl-D-aspartate (NMDA) type has a potentially wide range of therapeutic applications [19]. Functional inhibition of NMDA receptors can be achieved through actions at different recognition sites such as the primary transmitter site, strychnine-insensitive glycine site (glycine$_B$), polyamine site, and phencyclidine site located inside the cation channel. The NMDA receptor channel blockers act in an uncompetitive "use-dependent" manner, meaning that they usually only block the channel in the open state. This use-dependence has been interpreted by many to mean that stronger activation of the receptor should lead to a greater degree of antagonism. Such a mode of action has further been taken to imply that this class of antagonist may be particularly useful when overactivation of NMDA receptors can be expected, such as in epilepsy, ischaemia, and trauma. However, initial clinical experience with the selective, high affinity, strongly use-dependent uncompetitive NMDA receptor antagonist (+)-5-methyl-10,11-dihydro-5H-dibenzocyclohepten-5,10-imine maleate ((+)-MK-801) has been disappointing. Namely, therapeutic efficacy in epilepsy was poor while some psychotropic side effects were apparent at therapeutic doses. These observations, together with the fact that phencyclidine abusers experience similar psychotropic symptoms, has led to the conclusion that uncompetitive antagonism of NMDA receptors may not be a promising therapeutic approach.

However, the use of more elaborate electrophysiological methods indicates that there is no equality between different uncompetitive antagonists since factors such as the speed of receptor blockade (on-off kinetics) and the voltage-dependence of this effect may determine the pharmacodynamic features in vivo, i.e., therapeutic safety as well. Paradoxically, agents with low to moderate, rather than high, affinity may be desirable. Such findings triggered a reconsideration of the concept of uncompetitive antagonism of NMDA receptors in drug development [19, 22]. Uncompetitive NMDA receptor antagonists, such as amantadine and memantine—which fulfill the above criteria—have been used clinically for several years in the treatment of Parkinson's disease and dementia respectively, and do indeed rarely produce side effects at the therapeutic doses used in their respective indications.

In view of the above mentioned evidence, we have developed a series of novel uncompetitive NMDA receptor antagonists based on the unsaturated 1-aminoalkylcyclohexane structure. The present study was devoted to compare the NMDA receptor antagonistic properties of these unsaturated 1-aminoalkylcyclohexane derivatives in receptor-binding assays, electrophysiological experiments, one convulsion model and two models of motor impairment. The substitutions of these unsaturated 1-aminoalkylcyclohexanes are detailed in Table 6.

5-HT$_3$ Receptor Antagonists

5-HT$_3$ receptors are ligand gated ionotropic receptors permeable for cations. In man 5-HT$_3$ receptors show the highest density on enterochromaffin cells in the gastrointestinal mucosa, which are innervated by vagal afferents and the area postrema of the brain stem, which forms the chemoreceptor trigger zone.

Since 5-HT$_3$ receptors not only have a high density in the area postrema but also in the hippocampal and amygdala region of the limbic system, it has been suggested that 5-HT$_3$ selective antagonists may have psychotropic effects (Greenshaw & Silverstone, 1997).

Indeed, early animal studies suggested that the 5-HT$_3$ receptor antagonists, in addition to their well recognized anti-emetic use, may well be clinically useful in a number of areas. These include anxiety disorders, schizophrenia, drug and alcohol abuse disorders, depressive disorders, cognitive disorders, Alzheimer's disease, cerebellar tremor, Parkinson's disease treatment-related psychosis, pain (migraine and irritable bowel syndrome), and appetite disorders.

Neuronal Nicotinic Receptor Antagonists

At present, ten alpha subunits (alpha 1-10) and four beta (beta 1-4) subunits for nicotinic receptors are known. α4β2 receptors are probably the most common in the CNS, especially in the hippocampus and striatum. They form non-selective cation channels with slowly, incompletely desensitizing currents (type II). Homomeric α7 receptors are both pre- and postsynaptic and are found in the hippocampus, motor cortex and limbic system as well as in the peripheral autonomic nervous system. These receptors are characterized by their high Ca$^{2+}$ permeability and fast, strongly desensitizing responses (type 1A). Changes in nicotinic receptors have been implicated in a number of diseases. These include Alzheimer's disease, Parkinson's disease, Tourette's syndrome, schizophrenia, drug abuse, nicotine abuse, and pain.

Based on the observation that the nicotinic agonist nicotine itself seems to have beneficial effects, drug development so far aimed at the discovery of selective nicotinic agonists.

On the other hand, it is unclear whether the effects of nicotinic agonists in, e.g., Tourette's syndrome and schizophrenia, are due to activation or inactivation/desensitization of neuronal nicotinic receptors.

The effects of agonists on neuronal nicotinic receptors is strongly dependent on the exposure period. Rapid reversible desensitization occurs in milliseconds, rundown occurs in seconds, irreversible inactivation of α4β2 and α7 containing receptors occurs in hours and their upregulation occurs within days.

In other words: the effects of nicotinic "agonists" may in fact be due to partial agonism, inactivation and/or desensitization of neuronal nicotinic receptors. In turn, moderate concentrations of neuronal nicotinic receptor channel blockers could produce the same effects as reported for nicotinic agonists in the above mentioned indications.

THE PRESENT INVENTION

It has now been found that a range of unsaturated 1-aminoalkylcyclohexanes have pronounced and unexpected NMDA, 5HT$_3$, and nicotinic receptor antagonistic activity. Owing to the aforementioned property, the substances are suited for the treatment of a wide range of CNS disorders which involve disturbances of glutamatergic, serotoninergic, and nicotinic transmission, immunomodulatory effect, and anti-infectious diseases properties. These compounds are preferably in the form of a pharmaceutical composition thereof wherein they are present together with one or more pharmaceutically-acceptable diluents, carriers, or excipients.

OBJECTS OF THE INVENTION

It is an object of the present invention to provide novel pharmaceutical compounds which are unsaturated 1-aminoalkylcyclohexane NMDA, $5HT_3$, and nicotinic receptor antagonists and pharmaceutical compositions thereof. It is a further object of the invention to provide a novel method of treating, eliminating, alleviating, palliating, or ameliorating undesirable CNS disorders which involve disturbances of glutamatergic, serotoninergic, nicotinic transmission, for treating immunomodulatory disorders, and for treating infectious diseases by employing a compound of the invention or a pharmaceutical composition containing the same. An additional object of the invention is the provision of a process for producing the unsaturated 1-aminoalkylcyclohexane active principles. Yet additional objects will become apparent hereinafter, and still further objects will be apparent to one skilled in the art.

SUMMARY OF THE INVENTION

What we therefore believe to be comprised by our invention may be summarized inter alia in the following words:

A compound selected from those of formula I:

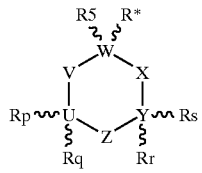

wherein:

R* is —$(A)_n$—$(CR^1R^2)_m$—$NR^3R^4$, n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$ is independently selected from the group consisting of linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, provided that U-V-W-X-Y-Z is selected from
cyclohexane,
cyclohex-2-ene,
cyclohex-3-ene,
cyclohex-1,4-diene,
cyclohex-1,5-diene,
cyclohex-2,4-diene, and
cyclohex-2,5-diene, and provided that at least one of $R_p$ and $R_q$, are not hydrogen and at least one of $R_r$, and $R_s$ are not hydrogen, and provided that when U-Z equals cyclohexane, then at least one of —$(A)_n$—$(CR^1R^2)_m$—, $R^3$, $R^4$, $R^5$, $R_p$, $R_q$, $R_r$, and $R_s$ is linear or branched lower alkenyl ($C_2$–$C_6$) or linear or branched lower alkynyl ($C_2$–$C_6$), and its optical isomers and pharmaceutically-acceptable acid or base addition salt thereof; such a method-of-treating a living animal for alleviation of a condition treatable by a NMDA antagonist comprising the step of administering to the living animal an amount of a compound selected from those of formula I:

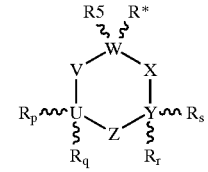

wherein:

R* is —$(A)_n$—$(CR^1R^2)_m$—$NR^3R^4$, n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:

cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of $-(A)_n-(CR^1R^2)_m-$, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; such a method-of-treating a living animal for alleviation of a condition wherein the compound is selected for its immunomodulatory, anti-malarial, anti-Borna virus, or anti-Hepatitis C, anti-trypanosomal, and anti-HSV efficacy, comprising the step of administering to the living animal an amount of a compound selected from those of formula I:

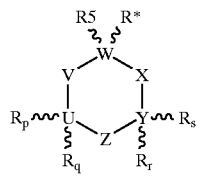

wherein:

R* is $-(A)_n-(CR^1R^2)_m-NR^3R^4$, n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R^s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, or $R_p$, $R_q$, $R_r$, and $R^s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:

cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of $-(A)_n-(CR^1R^2)_m-$, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; such a method-of-treating a living animal for alleviation of a condition treatable by an NMDA antagonist selected from the group consisting of excitotoxicity selected from ischaemia during stroke, trauma, hypoxia, hypoglycemia, glaucoma, and hepatic encephalopathy, chronic neurodegenerative diseases selected from Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, and Creutzfeldt-Jakob disease, other disorders related to long term plastic changes in the central nervous system selected from chronic pain, drug tolerance, dependence and addiction (e.g., opioids, cocaine, benzodiazepines, nicotine, and alcohol), and epilepsy, tardive dyskinesia, L-DOPA-induced dyskinesia, schizophrenia, anxiety, depression, acute pain, spasticity, and tinnitus, comprising the step of administering to the living animal an amount of a compound selected from those of formula I:

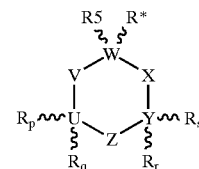

wherein:

R* is $-(A)_n-(CR^1R^2)_m-NR^3R^4$, n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R^s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group $R^*$ to form a double bond, or $R^5$ may combine with the carbon atom of W to which it is attached and an adjacent ring carbon atom to form a double bond, or $R_p$, $R_q$, $R^r$, and $R_s$ independently may combine with the carbon to which it is attached and the next adjacent carbon to form a double bond, or $R_p$, $R_q$, $R^r$, and $R_s$ independently may form a double bond with U or with Y to which it is attached, and provided that U-V-W-X-Y-Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of —$(A)_n$—$(CR^1R^2)_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; such a method-of-treating a living animal for alleviation of a condition treatable by a 5HT$_3$ receptor antagonist, comprising the step of administering to the living animal an amount of a compound selected from those of formula I:

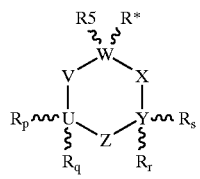

wherein:
$R^*$ is —$(A)_n$—$(CR^1R^2)_m$—$NR^3R^4$,
n+m=0, 1, or 2,
A is selected from the group consisting of linear or branched lower alkyl ($C_1$–$C_6$), linear or branched lower alkenyl ($C_2$–$C_6$), and linear or branched lower alkynyl ($C_2$–$C_6$),
$R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group $R^*$ to form a double bond, or $R^5$ may combine with the carbon atom of W to which it is attached and an adjacent ring carbon atom to form a double bond, or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of —$(A)_n$—$(CR^1R^2)_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; such a method-of-treating a living animal for alleviation of a condition treatable by a neuronal nicotinic receptor antagonist, comprising the step of administering to the living animal an amount of a compound selected from those of formula I:

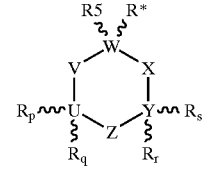

wherein
$R^*$ is —$(A)_n$—$(CR^1R^2)_m$—$NR^3R^4$,
N+m=0, 1, or 2,
A is selected from the group consisting of linear or branched lower alkyl ($C_1$–$C_6$), linear or branched lower alkenyl ($C_2$–$C_6$), and linear or branched lower alkenyl ($C_2$–$C_6$),
$R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$),
$R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double band with U or with Y to which it is attached, and provided that U-V-W-X-Y-Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of —(A)$_n$—(CR$^1$R$^2$)$_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; such a method-of-treating a living animal for alleviation of a condition treatable by a 5HT$_3$ antagonist selected from the group consisting of anxiety disorders, depressive disorders, Schizophrenia and treatment related psychosis, drug and alcohol abuse disorders, cognitive disorders, Alzheimer's disease, Parkinson's disease, cerebellar tremor, migraine, appetite disorders, inflammatory bowel syndrome (IBS), and emesis, comprising the step of administering to the living animal an amount of a compound selected from those of formula I:

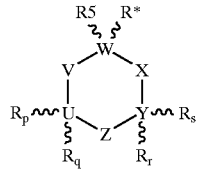

wherein:
R* is —(A)$_n$—(CR$^1$R$^2$)$_m$—NR$^3$R$^4$,
n+m=0, 1, or 2,
A is selected from the group consisting of linear or branched lower alkyl ($C_1$–$C_6$), linear or branched lower alkenyl ($C_2$–$C_6$), and linear or branched lower alkynyl ($C_2$–$C_6$),
$R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of —(A)$_n$—(CR$^1$R$^2$)$_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; such a method-of-treating a living animal for alleviation of a condition treatable by a neuronal nicotinic receptor antagonist selected from the group consisting of Tourette's syndrome, anxiety disorders, Schizophrenia, drug abuse, nicotine abuse, cocaine abuse, dyskinesia (Morbus Huntington, L-DOPA-induced), attention deficit hyperactivity disorder (ADHD), Alzheimer's disease, Parkinson's disease, and pain, comprising the step of administering to the living animal an amount of a compound selected from those of formula I:

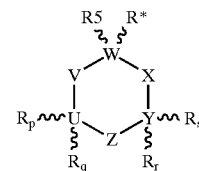

wherein:
R* is —(A)$_n$—(CR$^1$R$^2$)$_m$—NR$^3$R$^4$,
n+m=0, 1, or 2,
A is selected from the group consisting of linear or branched lower alkyl ($C_1$–$C_6$), linear or branched lower alkenyl ($C_2$–$C_6$), and linear or branched lower alkynyl ($C_2$–$C_6$),
$R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U-Z equals cyclohexane, then at least one of —(A)$_n$—(CR$^1$R$^2$)$_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition; and such a pharmaceutical composition having a compound selected from those of formula I:

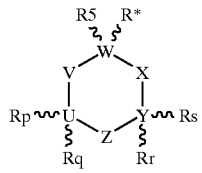

wherein:
R* is —(A)$_n$—(CR$^1$R$^2$)$_m$—NR$^3$R$^4$,
n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$ is independently selected from the group consisting of linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group R* to form a double bond, or $R^5$ may combine with the carbon atom of W to which it is attached and an adjacent ring carbon atom to form a double bond, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, provided that U-V-W-X-Y-Z is selected from
cyclohexane,
cyclohex-2-ene,
cyclohex-3-ene,
cyclohex-1,4-diene,
cyclohex-1,5-diene,
cyclohex-2,4-diene, and
cyclohex-2,5-diene, and provided that at least one of $R_p$ and $R_q$, are not hydrogen and at least one of $R_r$, and $R_s$ are not hydrogen, and provided that when U-Z equals cyclohexane, then at least one of —(A)$_n$—(CR$^1$R$^2$)$_m$—, $R^3$, $R^4$, $R^5$, $R_p$, $R_q$, $R_r$ and $R_s$ is linear or branch lower alkenyl ($C_2$–$C_6$) or linear or branched lower alkynyl ($C_2$–$C_6$), in combination with one or more pharmaceutically-acceptable diluents, excipients, or carriers.

DETAILED DESCRIPTION OF THE INVENTION

The following details and detailed Examples are given by way of illustration only, and are not to be construed as limiting.

Scheme: Examples 1 and 2

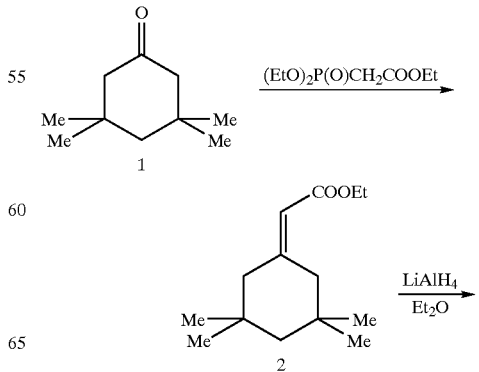

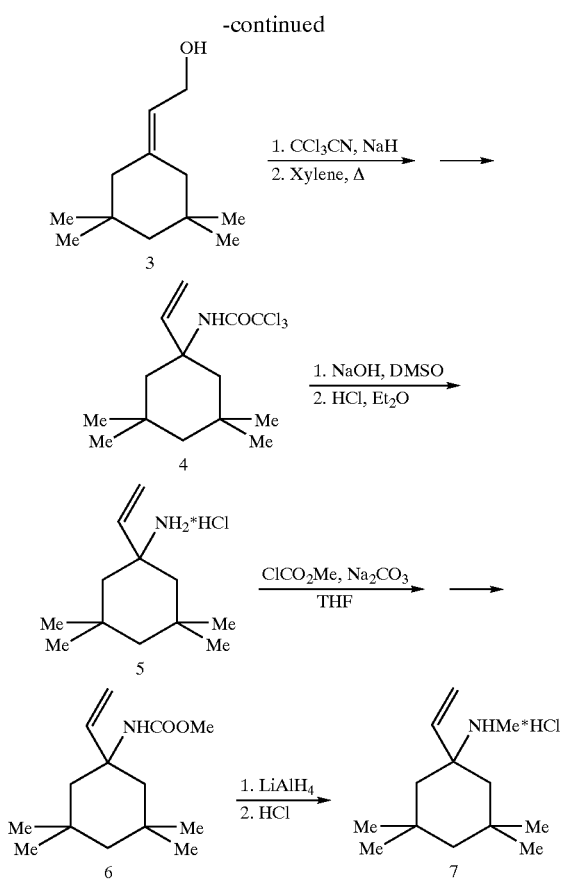

EXAMPLE 1

3,3,5,5-Tetramethyl-1-vinylcyclohexanamine hydrochloride (5)

a) Ethyl 2-(3,3,5,5-tetramethylcyclohexylidene)acetate (2).

To a stirred solution of triethyl phosphonoacetate (49.32 g, 222 mmol) in dry THF (180 ml) under argon NaH (8.8 g, 222 mmol, 60% suspension in mineral oil) was added in small portions while cooling with ice water. Stirring was continued for 1 h at room temperature, then a solution of 3,3,5,5-tetramethylcyclohexanone (30.85 g, 200 mmol) was added over 10 min and the resulting mixture was refluxed for 22 h. It was then poured onto ice (400 g) and the product was extracted with diethyl ether (4150 ml), and the extracts dried over MgSO$_4$. After solvent evaporation in vacuo an oily residue was distilled at 145° C. (11 mm Hg) to give 36.8 g (86%) of 2 as an oil. $^1$H NMR (CDCl$_3$, TMS): 0.96 and 0.98 (total 12H, both s, 3,5-CH$_3$); 1.27 (3H, t, CH$_3$-ethyl); 1.33 (2H, m, 4-CH$_2$); 1.95 and 2.65 (total 4H, both s, 2,6-CH$_2$); 4.14 (2H, q, CH$_2$-ethyl) and 5.69 ppm (1H, s, =C—H).

b) 2-(3,3,5,5-Tetramethylcyclohexylidene)ethanol (3).

To a stirred solution of LiAlH$_4$ (1.7 g, 45 mmol) in dry ether (60 ml) a solution of acetate 2 (3.2 g, 15 mmol) in ether (20 ml) was added dropwise while cooling with ice water. Stirring was continued for 1 h and the residual LiAlH$_4$ was destroyed with water. The aqueous layer was separated and twice extracted with ether (30 ml). The combined extracts were washed with brine (50 ml) and dried over MgSO$_4$. After concentration in vacuo an oily residue was purified by Kugelrohr short path distillation (150–170° C., 11 mm Hg) to give 3 (2.3 g, 89%) as an oil. $^1$H NMR (CDCl$_3$, TMS): 0.92 (6H, s, 3,5-CH$_3$); 1.10 (1H, br s, OH); 1.28 (2H, s, 4-CH$_2$); 1.87 and 1.94 (total 4H, both s, 2,6-CH$_2$); 4.16 (2H, d, 7 Hz, CH$_2$O) and 5.50 ppm (1H, t, 7 Hz, =C—H).

c) 2,2,2-Trichloro-N-(3,3,5,5-tetramethyl-1-vinylcyclohexyl)acetamide (4).

To a solution of alcohol 3 (0.8 g, 4.7 mmol) in diethyl ether (5 ml) NaH (0.22 g of a 55% dispersion in mineral oil (0.22 mmol)) was added. The reaction mixture was cooled to −10° C. and a solution of trichloroacetonitrile (0.68 g, 4.7 mmol) in diethyl ether (3 ml) was added dropwise. The solution was allowed to warm to room temperature and the solvent evaporated. Pentane (8 ml) containing methanol (0.018 ml) was added to the residue. The resulting mixture was filtered through a pad of celite and evaporated. The residual oil was dissolved in xylene (10 ml) and refluxed for 10 h. Main amount of xylene was distilled off at reduced pressure (11 mm Hg) and the residue purified by flash chromatography on silica gel (hexane, hexane-ethyl acetate, 10:1) to give 4 (0.98 g, 66%) as an oil. $^1$H NMR (CDCl$_3$, TMS): 0.95 (6H, s, 3,5-CH$_3$); 1.18 (6H, s, 3,5-CH$_3$); 1.1–1.5 (2H, m, 4-CH$_2$); 1.32 (2H, d, 15 Hz, 2,6-CH$_2$); 2.15 (2H, d, 15 Hz, 2,6-CH$_2$); 5.08 (1H, d, 11 Hz, =CH$_2$); 5.13 (1H, d, 18 Hz, =CH$_2$); 5.85 (1H, dd, 18 and 11 Hz, —HC=) and 6.7 ppm (1H, br s, NH).

d) 3,3,5,5-Tetramethyl-1-vinylcyclohexanamine hydrochloride (5).

A mixture of amide 4 (0.32 g, 1 mmol) and powdered NaOH (0.4 g, 10 mmol) in DMSO (3 ml) was stirred for 7 days at room temperature. The reaction mixture was diluted with H$_2$O (20 ml) and stirred overnight at room temperature. The product was extracted with hexane (310 ml). The combined extracts were washed with brine (20 ml), dried over NaOH and filtered through a pad of celite. To the solution obtained 4 M HCl in dry ethyl ether (0.5 ml) was added and the solvent was evaporated. The residue was treated with acetonitrile (10 ml) and the precipitate was collected on a filter and dried over P$_2$O$_5$ in vacuo to give 5 (0.12 g, 53%) as a colorless solid. $^1$H NMR (CDCl$_3$, TMS): 0.98 and 1.01 (total 12H, both s, 3,5-CH$_3$); 1.19 and 1.29 (total 2H, both d, 14 Hz, 4-CH$_2$); 1.62 (2H, d, 13.5 Hz, 2,6-CH$_2$); 1.72 (2H, br s, H$_2$O); 2.16 (2H, d, 13.5 Hz, 2,6-CH$_2$); 5.46 and 5.73 (2H, both d, 18 and 11 Hz, =CH$_2$); 6.16 (1H, dd, 18 and 11 Hz, =CH) and 8.24 ppm (3H, br s, NH$_3^+$).

EXAMPLE 2

N,3,3,5,5-Pentamethyl-1-vinylcyclohexylamine hydrochloride (7)

a) Methyl 3,3,5,5-tetramethyl-1-vinylcyclohexylcarbamate (6).

A mixture of amine hydrochloride 5 (0.25 g, 1.2 mmol) and Na$_2$CO$_3$ (0.73 g, 6.9 mmol) in THF (6 ml) was stirred at room temperature for 1 h. Methyl chloroformate (0.27 ml, 3.45 mmol) was added and the reaction mixture was stirred at room temperature for 15 h. The mixture was diluted with diethyl ether (20 ml), filtered and evaporated to the dryness. The crude product was purified by flash chromatography on silica gel (light petroleum ether-ethyl acetate, 10:1) to give 6 (0.24 g, 87%) as a colorless solid with m.p. 61–63° C. $^1$H-NMR (CDCl$_3$, TMS): 0.92 and 1.15 (total 12H, both s, 3,5-CH$_3$); 1.00–1.40 (4H, m, 4-CH$_2$ and 2,6-CH); 2.00 (2H, d, 14 Hz, 2,6-CH); 3.62 (3H, s, CH$_3$N); 4.72 (1H, br s, NH); 5.00 and 5.06 (total 2H, both d, 10.5 and 17 Hz, =CH$_2$) and 5.83 ppm (1H, dd, 10.5 and 17 Hz, =CH).

b) N,3,3,5,5-Pentamethyl-1-vinylcyclohexylamine hydrochloride (7).

A mixture of LiAlH$_4$ (0.28 g, 7.4 mmol) and carbamate 6 (0.22 g, 0.92 mmol) in THF (22 ml) was refluxed for 12 h. Then it was cooled in an ice bath and water (20 ml) was added dropwise. The resulting suspension was extracted with hexane (320 ml) and the combined extracts were washed with brine (20 ml). The extract was dried over NaOH, filtered and treated with 2.4 M HCl solution in diethyl ether (1 ml). The resulting suspension was evaporated to the dryness. The residue was treated with diethyl ether (10 ml) and acetonitrile (1 ml). The precipitate was collected on a filter and dried in vacuo over $P_2O_5$ to give 7 (0.11 g, 52%) as a colorless solid. $^1$H-NMR (CDCl$_3$, TMS): 1.00 and 1.02 (total 12H, both s, 3,5-CH$_3$); 1.23 and 1.32 (total 2H, both d, 15 Hz, 4-CH$_2$); 1.72 (2H, d, 13 Hz, 2,6-CH); 2.15 (2H, d, 13 Hz, 2,6-CH); 2.45 (3H, t, 5 Hz, CH$_3$N); 5.64 and 5.69 (total 2H, both d, 11 and 17 Hz, =CH$_2$); 5.98 (1H, dd, 11 and 17 Hz, =CH) and 9.30 ppm (2H, br s, NH$_3^+$).

Scheme: Examples 3 and 4

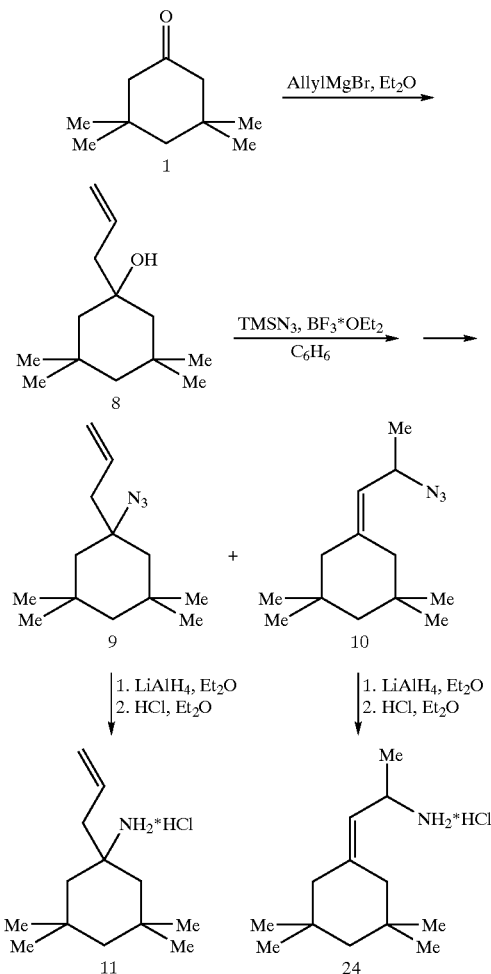

EXAMPLE 3

1-Allyl-3,3,5,5-tetramethylcyclohexanamine hydrochloride (11)

a) 1-Allyl-3,3,5,5-tetramethylcyclohexanol (8).

To a stirred 1 M etheral solution of allyllmagnesium bromide (60 ml, 60 mmol) was added dropwise a solution of 3,3,5,5-tetramethylcyclohexanone (3.86 g, 25 mmol) in dry ether (20 ml). The mixture was stirred for 1 h at ambient temperature and boiled at reflux for 10 min. Then it was cooled with ice water and carefully treated with saturated aqueous NH$_4$Cl (40 ml). The organic layer was separated and washed with water and brine. After drying over anhydrous MgSO$_4$, the solution was concentrated in vacuo. The residue was fractionally distilled at reduced pressure to give 3.5 g (72%) of 8 with b.p. 98–100° C./12 mm Hg. $^1$H NMR (CDCl$_3$, TMS): 0.88 (6H, s, 3,5-CH$_{3eq}$); 1.20 (6H, s, 3,5-CH$_{3ax}$); 0.95–1.60 (6H, m, 2,4,6-CH$_2$); 2.15 (2H, d, 7.5 Hz, CH$_2$C=); 4.95–5.30 (2H, m, =CH$_2$) and 5.65–6.20 ppm (1H, m, =CH).

b) 1-Allyl-1-azido-3,3,5,5-tetramethylcyclohexane (9) and 1-Methyl-2-(3,3,5,5-tetramethylcyclohexylidene)ethyl azide (10).

To a solution of cyclohexanol 8 (1.96 g, 10 mmol) in dry benzene (20 ml) under argon was added azidotrimethylsilane (12 mmol). To this cooled (5° C.) solution was slowly added BF$_3$*OEt$_2$ (12 mmol) via syringe within 20 min. The mixture was stirred for 6 h, then water was slowly added. The organic layer was separated and washed with saturated aqueous NaHCO$_3$, and with brine, and dried over MgSO$_4$. Filtration and evaporation of the solvent keeping the temperature below 25° C. gave an oil which was separated by column chromatography on silica gel (light petroleum ether). A fraction with Rf 0.85 (hexane) was collected. Evaporation of the solvent provided 9 as a colorless oil (0.26 g, 11.7%). $^1$H NMR (CDCl$_3$, TMS): 0.89 (6H, s, 3,5-CH$_{3eq}$); 0.90 (1H, d, 14 Hz, 4-CH$_{ax}$); 1.05 (2H, d, 14 Hz, 2,6-CH$_{ax}$); 1.18 (6H, s, 3,5-CH$_{3ax}$); 1.37 (1H, d, 14 Hz, 4-CH$_{eq}$); 1.60 (2H, d, 14 Hz, 2,6-CH$_{eq}$), 2.29 (2H, d, 7 Hz, CH$_2$C=); 4.95–5.25 (2H, m, =CH$_2$) and 5.65–6.15 ppm (1H, m, =CH).

Evaporation of additional fraction (Rf 0.65 (hexane)) gave 0.425 g (20.3%) of azide 10 as a colorless oil. $^1$H NMR (CDCl$_3$, TMS): 0.91 (6H, s), 0.94 (3H, s) and 0.96 (3H, s, 3',5'-CH$_3$); 1.23 (3H, d, 6.5 Hz, 1-CH$_3$); 1.26 (2H, s, 4'-CH$_2$); 1.89 (2H, s) and 1.96 (2H, s, 2',6'-CH$_2$); 4.31 (1H, dq, 6.5 and 9.5 Hz, 1-CH) and 5.21 ppm (1H, dm, 9.5 Hz, =CH).

c) 1-Allyl-3,3,5,5-tetramethylcyclohexanamine hydrochloride (11).

A solution of azide 9 (0.221 g, 1.0 mmol) in dry ether (4 ml) was added dropwise to a stirred suspension of lithium aluminum hydride (0.152 g, 4 mmol) in ether (10 ml) within 10 min. The mixture was stirred for 4 h, then it was treated with 20% aqueous NaOH (8 ml). The aqueous layer was separated and extracted with diethyl ether (215 ml). The combined organic extracts were washed with brine and dried over NaOH. The filtered solution was treated with dry HCl solution in diethyl ether and evaporated. Dry diethyl ether was added to the solid residue and it was collected on filter, and washed with dry ether to give 11 (0.105 g, 47%) as a colorless solid. $^1$H NMR (CDCl$_3$, TMS): 1.03 (6H, s, 3,5-CH$_{3eq}$); 1.06 (6H, s, 3,5-CH$_{3ax}$); 1.29 (2H, s, 4-CH$_2$); 1.63 (2H, d, 13 Hz, 2,6-CH$_{ax}$); 1.80 (2H, d, 13 Hz, 2,6-CH$_{eq}$), 2.71 (2H, d, 7 Hz, CH$_2$C=); 5.10–5.40 (2H, m, =CH$_2$); 5.75–6.25 (1H, m, =CH) and 8.25 ppm (3H, br s, NH$_3^+$).

EXAMPLE 4

1-(3,3,5,5-Tetramethylcyclohexylidene)-2-propanamine hydrochloride (24)

A solution of 1-methyl-2-(3,3,5,5-tetramethylcyclohexylidene)ethyl azide (10) (0.33 g, 1.5 mmol) in dry diethyl ether (4 ml) was added dropwise to a stirred suspension of lithium aluminum hydride (0.152 g, 4 mmol) in ether (15 ml) within 10 min. The mixture was stirred for 4 h, then it was treated with 20% aqueous NaOH (8 ml). The aqueous layer was extracted with ether (2*15 ml). The organic extracts were combined, washed with brine and dried over NaOH. The filtered solution was treated with dry HCl solution in ether and evaporated in vacuo. Dry ether was added to the solid residue and it was collected on filter and washed with dry ether to give 24 (0.18 g, 54%) as a colorless solid. $^1$H NMR (CDCl$_3$, TMS): 0.89 (6H, s), 0.92 (3H, s) and 0.98 (3H, s, 3',5'-CH$_3$); 1.27 (2H, s, 4'-CH$_2$); 1.47 (3H, d, 6.5 Hz, 3-CH$_3$); 1.84 (1H, d, 13.5 Hz, 2'-CH); 1.87 (2H, s, 6'-CH$_2$), 2.06 (1H, d, 13.5 Hz, 2'-CH); 4.17 (1H, dq, 6.5 and 9.5 Hz, 2-CH); 5.35 (1H, d, 9.5 Hz, =CH) and 8.25 ppm (3H, br s, NH$_3^+$).

m, 2',6'-CH$_{ax}$ and piperidine 3,5-CH, 4-CH$_2$,); 2.37 (2H, d, 13.4 Hz, 2',6'-CH$_{eq}$); 2.40–2.70 (2H, m, piperidine 3,5-CH); 2.76 (2H, d, 7.2 Hz, CH$_2$C=); 2.75–3.00 (2H, m, piperidine 2,6-CH); 3.64 (2H, d, 11.6 Hz, piperidine 2,6-CH); 5.13 (1H, d, 9.6 Hz) and 5.24 (1H, d, 17.8 Hz, =CH$_2$); 5.85–6.15 (1H, m, =CH) and 10.72 ppm (1H, br s, NH).

EXAMPLE 6

1-[3,3,5,5-Tetramethyl-1-(3-methyl-2-butenyl) cyclohexyl]piperidine hydrochloride (14)

Prepared from piperidine 12 according to the procedure for compound 13 (Example 5, b) using 4-bromo-2-methyl-

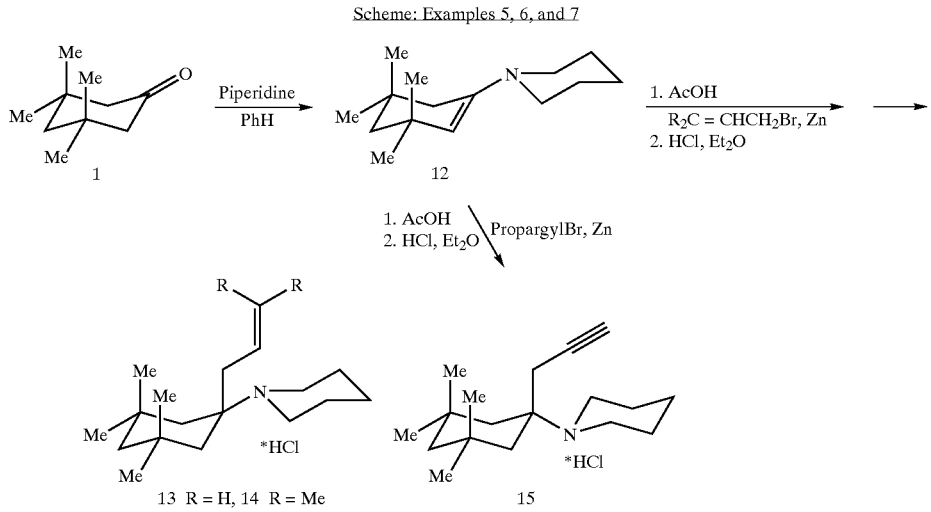

EXAMPLE 5

1-(1-Allyl-3,3,5,5-tetramethylcyclohexyl)piperidine hydrochloride (13)

a) 1-(3,3,5,5-Tetramethyl-1-cyclohexenyl-1)piperidine (12).

Prepared by condensation of piperidine (1.2 equivalents) and 3,3,5,5-tetramethylcyclohexanone by heating in benzene with azeotropic removal of water. Crude product was obtained by removing starting materials at vacuum distillation conditions (100° C./10 mm Hg). Amber oil. $^1$H NMR (CDCl$_3$, TMS): 0.94 (6H, s) and 0.97 (6H, s, 3',5'-CH$_3$); 1.25 (2H, s, 4'-CH$_2$); 1.40–1.70 (6H, m, piperidine 3,4,5-CH$_2$); 1.76 (2H, s, 6'-CH$_2$); 2.60–2.85 (4H, m, piperidine 2,6-CH$_2$) and 4.40 ppm (1H, s, =CH).

b) 1-(1-Allyl-3,3,5,5-tetramethylcyclohexyl)piperidine hydrochloride (13).

To a solution of enamine 12 (2.1 g, 9 mmol) in THF (20 ml) was added acetic acid 0.675 g, 11.25 mmol). The mixture was stirred for 5 min and zinc powder (0.74 g, 11.25 mgA) was added. Then a solution of allylbromide (1.63 g, 13.5 mmol) in THF (5 ml) was added dropwise and the mixture was stirred at ambient temperature for 6 h. Aqueous Na$_2$CO$_3$ was added and the resulting mixture was extracted with ether. The extract was washed with brine, dried over anhydrous MgSO$_4$, and concentrated in vacuo. The residue was separated by column chromatography on silica gel (hexane, 5% EtOAc in hexane). The fraction with Rf 0.85 (hexane-EtOAc, 13:2) was collected, evaporated and treated with dry HCl solution in ether. The precipitate was filtered and washed with hexane-EtOAc mixture to give 13 (0.79 g, 29%) as a colorless solid. $^1$H NMR (CDCl$_3$, TMS): 1.07 (6H, s, 3',5'-CH$_{3eq}$), 1.10 (6H, s, 3',5'-CH$_{3ax}$); 1.34 (1H, d, 12.2 Hz) and 1.45 (1H, d, 12.2 Hz, 4'-CH$_2$); 1.70–1.95 (6H, 2-butene instead of allylbromide. Yield: 20%. $^1$H NMR (CDCl$_3$, TMS): 1.07 and 1.08 (total 12H, both s, 3',5'-CH$_3$), 1.32 and 1.44 (2H, both d, 14.2 Hz, 4'-CH$_2$); 1.69 and 1.76 (6H, both s, =C(CH$_3$)$_2$); 1.68–1.96 (4H, m, 3,5-CH and 4-CH$_2$,); 1.84 (2H, d, 13.4 Hz, 2',6'-CH$_{ax}$); 2.31 (2H, d, 13.4 Hz, 2',6'-CH$_{eq}$); 2.40–2.80 (4H, m, N(CH)$_2$, 3,5-CH); 2.60 (2H, d, 7.2 Hz, CH$_2$C=); 3.63 (2H, d, 10.4 Hz, N(CH)$_2$); 5.31 (1H, t, 6.8 Hz, =CH) and 10.55 ppm (1H, br s, NH).

EXAMPLE 7

1-[3,3,5,5-Tetramethyl-1-(2-propynyl)cyclohexyl] piperidine hydrochloride (15)

Prepared from piperidine 12 according to the procedure for compound 13 (Example 5, b) using 3-bromopropyne instead of allylbromide. Yield: 6%. $^1$H NMR (CDCl$_3$, TMS): 1.07 (6H, s, 3',5'-CH$_{3eq}$), 1.11 (6H, s, 3',5'-CH$_{3ax}$); 1.23 and 1.44 (total 2H, both d, 14.3 Hz, 4'-CH$_2$); 1.75–2.00 (4H, m, piperidine 3,5-CH, 4-CH$_2$,); 1.91 (2H, d, 13.2 Hz, 2',6'-CH$_{ax}$); 2.28 (1H, s, HCC); 2.34 (2H, d, 13.2 Hz, 2',6'-CH$_{eq}$); 2.40–2.70 (2H, m, piperidine 3,5-CH); 2.81 (2H, s, CH$_2$CC); 2.85–3.10 (2H, m, piperidine 2,6-CH); 3.69 (2H, d, 10.2 Hz, piperidine 2,6-CH) and 11.12 ppm (1H, br s, NH).

Scheme: Examples 8 and 9

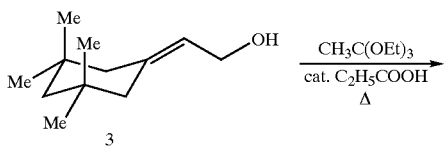

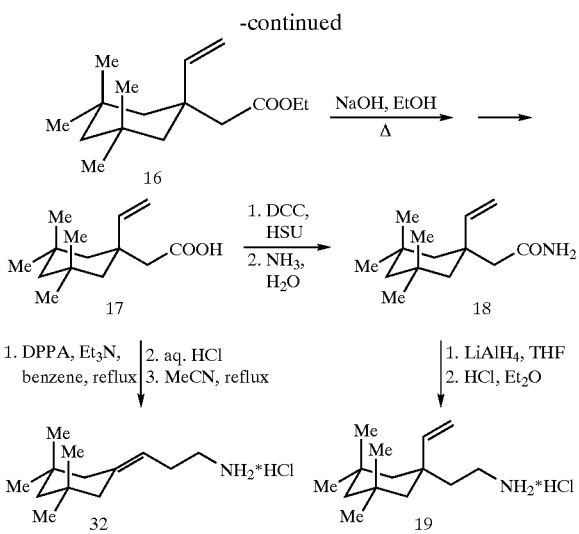

EXAMPLE 8

2-(3,3,5,5-Tetramethyl-1-vinylcyclohexyl) ethanamine hydrochloride (19)

a) Ethyl 2-(3,3,5,5-tetramethyl-1-vinylcyclohexyl)acetate (16).

A mixture of triethyl orthoacetate (18.6 ml, 102 mmol), 2-(3,3,5,5-tetramethyl-cyclohexylidene)ethanol (3) (4.63 g, 25.4 mmol) and propionic acid (0.19 ml, 2.5 mmol) was heated at 145° C. for 10 h. Ethanol was distilled off from the mixture in the course of reaction. The reaction mixture was cooled and poured into water (100 ml). The aqueous phase was extracted with hexane (250 ml) and the combined organic phases were washed with 5% aqueous $KHSO_4$ (50 ml) and brine (50 ml). The extract was dried over $MgSO_4$, filtered and evaporated. The residue was purified by flash chromatography on silica gel (light petroleum ether and light petroleum ether-ethyl acetate, 100:2) to give 16 (4.64 g, 73%) as an oil. $^1$H-NMR ($CDCl_3$, TMS): 0.91 (6H, s, 3,5-$CH_3$); 1.01 (6H, s, 3,5-$CH_3$); 1.23 (3H, t, 7 Hz, ethyl $CH_3$) 1.00–1.30 (4H, m, 4-$CH_2$ and 2,6-CH); 1.86 (2H, d, 13 Hz, 2,6-CH); 2.22 (2H, s, $CH_2$C=O); 4.08 (2H, q, 7 Hz, ethyl $CH_2$); 5.06 and 5.07 (total 2H, both d, 11 and 17.5 Hz, =$CH_2$) and 5.95 ppm (1H, dd, 11 and 17.5 Hz, —CH=).

b) 2-(3,3,5,5-Tetramethyl-1-vinylcyclohexyl)acetic acid (17).

A solution of NaOH (1.03 g, 25.8 mmol) and acetate 16 (1.3 g, 5.15 mmol) in methanol (26 ml) was refluxed for 3 h. The mixture was cooled to room temperature and poured into water (100 ml). The aqueous phase was acidified by conc. aqueous HCl and extracted with hexane (330 ml). The combined organic phases were washed with brine and dried over $CaCl_2$, filtered and evaporated. The residue was purified by flash chromatography on silica gel (light petroleum ether-ethyl acetate, 10:1) to give 17 (0.7 g, 71%) as a colorless solid with m.p. 92–94° C. $^1$H-NMR ($CDCl_3$, TMS): 0.92 (6H, s, 3,5-$CH_3$); 1.02 (6H, s, 3,5-$CH_3$); 1.00–1.30 (4H, m, 4-$CH_2$ and 2,6-CH); 1.90 (2H, d, 14 Hz, 2,6-CH); 2.27 (2H, s, $CH_2$C=O); 5.11 and 5.13 (total 2H, both d, 11 and 18 Hz, =$CH_2$); 5.99 (1H, dd, 18 and 11 Hz, =CH) and 10.80 ppm (1H, br s, COOH).

c) 2-(3,3,5,5-Tetramethyl-1-vinylcyclohexyl)acetamide (18).

N-Hydroxysuccinimide (0.25 g, 2.2 mmol) and N,N'-dicyclohexyl carbodiimide (0.45, 2.2 mmol) was added to a solution of cyclohexylacetic acid 17 (0.45 g, 2 mmol) in THF (5 ml). The mixture was stirred for 18 h at room temperature and cooled in an ice bath. 25% aqueous $NH_4OH$ (2 ml) was added in one portion and the mixture was stirred at room temperature for 2 h. The precipitate was filtered off and washed with diethyl ether (30 ml). The organic phase of filtrate was separated and washed with 5% aqueous $KHSO_4$ (10 ml) and brine. The extract was dried over $MgSO_4$, filtered and evaporated. The residue was purified by flash chromatography on silica gel (light petroleum ether-ethyl acetate, 4:1 to 1:1) to give 18 (0.34 g, 76%) as a colorless solid with m.p. 44–46° C. $^1$H-NMR ($CDCl_3$, TMS): 0.91 (6H, s, 3,5-$CH_3$); 1.02 (6H, s, 3,5-$CH_3$); 1.00–1.30 (4H, m, 4-$CH_2$ and 2,6-CH); 1.85 (2H, d, 14 Hz, 2,6-CH); 2.13 (2H, s, $CH_2$C=O); 5.18 and 5.19 (total 2H, both d, 18 and 11 Hz, =$CH_2$); 5.40 and 5.60 (total 2H, both br s, $NH_2$) and 6.03 ppm (1H, dd, 18 and 11 Hz, =CH).

d) 2-(3,3,5,5-Tetramethyl-1-vinylcyclohexyl)ethanamine hydrochloride (19).

The mixture of $LiAlH_4$ (0.41 g, 11 mmol) and amide 18 (0.30 g, 1.4 mmol) in THF (18 ml) was refluxed for 17 h. Then it was cooled in an ice bath and water (30 ml) was added dropwise. The resulting suspension was extracted with hexane (330 ml) and the combined organic phases were washed with brine. The extract was dried over NaOH, filtered and concentrated to ~10 ml volume. 4.8 M HCl solution in diethyl ether (1 ml) was added and the resulting suspension was evaporated to the dryness. The residue was treated with acetonitrile (5 ml) and the precipitate was collected on filter and dried in vacuo over NaOH to give 19 (0.16 g, 50%) as a colorless solid. $^1$H-NMR ($CDCl_3$, TMS): 0.89 (6H, s, 3,5-$CH_3$); 1.02 (6H, s, 3,5-$CH_3$); 0.90–1.80 (8H, m, ring protons and ethanamine-2-$CH_2$); 2.92 (2H, br s, $CH_2$N); 5.05 and 5.15 (2H, both d, 18 and 11 Hz, =$CH_2$); 5.77 (1H, dd, 18 and 11 Hz, =CH) and 8.10 ppm (3H, br s, $NH_3^+$).

EXAMPLE 9

3-(3,3,5,5-Tetramethylcyclohexylidene)propanamine hydrochloride (32)

Triethylamine (0.25 ml, 1.76 mmol) and diphenylphosphoryl azide (0.38 ml, 1.76 mmol) was added to a solution of acid 17 (0.36 g, 1.6 mmol) in benzene (6 ml). The mixture was refluxed for 2 h, cooled to room temperature and evaporated to the dryness. Cold (~5° C.) conc. aqueous HCl (3 ml) was added to the residue. The resulting mixture was stirred at room temperature for 18 h and made strongly alkaline by addition of 10% aqueous NaOH. Hexane (20 ml) was added to the mixture and both phases filtered. The precipitate was washed with hexane (25 ml) and water (25 ml). The organic phase of the filtrate was separated. The aqueous phase was washed with hexane (210 ml). The combined organic phases were washed with brine (10 ml), dried over NaOH and filtered. 4.8 M HCl solution in diethyl ether (1 ml) was added and the resulting suspension was evaporated. The residue was recrystallized from acetonitrile and dried in vacuo over $P_2O_5$ to give 32 (0.1 g, 43%) as a colorless solid. $^1$H-NMR: ($CDCl_3$, TMS): 0.90 and 0.92 (total 12H, both s, c-Hex-3,5-$CH_3$); 1.23 (2H, s, c-Hex-4-$CH_2$); 1.86 and 1.92 (total 4H, both s, c-Hex-2,6-$CH_2$); 2.49 (2H, q, 7 Hz, propanamine-2-$CH_2$); 2.98 (2H, t, 7 Hz, propanamine-1-$CH_2$); 5.15 (1H, t, 7 Hz, =CH—) and 8.30 ppm (3H, br s, $NH_3^+$).

Scheme: Examples 10 and 11

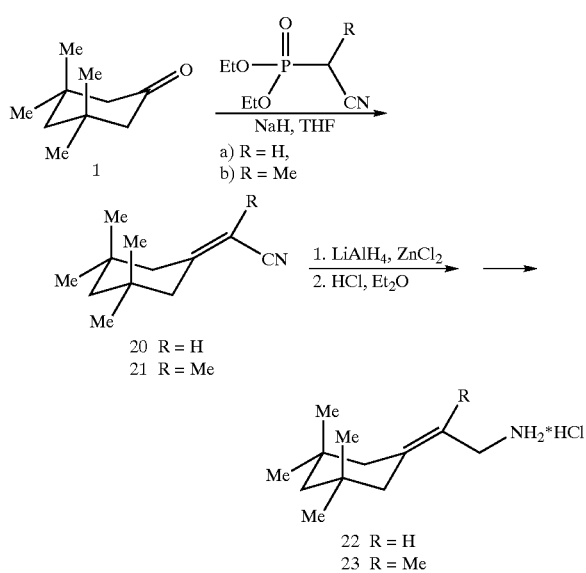

EXAMPLE 10

2-(3,3,5,5-Tetramethylcyclohexylidene)ethanamine hydrochloride (22)

a) 3,3,5,5-Tetramethylcyclohexylideneacetonitrile (20).

60% NaH dispersion in mineral oil (0.96 g, 24 mmol) was added to a solution of diethyl cyanomethylphosphonate (4.25 g, 24 mmol) in THF (30 ml) while cooling with ice water. The mixture was stirred for 30 min and a solution of 3,3,5,5-tetramethylcyclohexanone (3.08 g, 20 mmol) in THF (10 ml) was added dropwise. Cooling bath was removed and the mixture was stirred at room temperature for 72 h. It was poured into ice water (100 ml) and extracted with diethyl ether (350 ml). The combined organic phases were washed with brine, dried over MgSO$_4$, filtered and evaporated. The crude product was purified by flash chromatography on silica gel (light petroleum ether-ethyl acetate, 10:1) to give 20 (2.38 g, 71%) as a colorless oil. $^1$H-NMR (CDCl$_3$, TMS):0.97 and 1.01 (total 12H, both s, 3',5'-CH$_3$); 1.36 (2H, s, 4'-CH$_2$); 2.01 (2H, s, 2'-CH$_2$); 2.26 (2H, s, 6'-CH$_2$) and 5.14 ppm (1H, s, =CH).

b) 2-(3,3,5,5-Tetramethylcyclohexylidene)ethanamine hydrochloride (22).

A suspension of LiAlH$_4$ (0.68 g, 18 mmol) in diethyl ether (30 ml) was cooled in an ice bath and 1M ZnCl$_2$ solution in diethyl ether (9 ml, 9 mmol) was added. The resulting mixture was stirred for 15 min and a solution of nitrile 20 (1 g, 6 mmol) in diethyl ether (30 ml) was added dropwise keeping the temperature at 0–5° C. Ice bath was then removed and the mixture was stirred at room temperature for 24 h. Water (30 ml) and 20% aqueous NaOH (20 ml) was added while cooling with an ice bath. The aqueous phase was extracted with diethyl ether (450 ml). The combined organic phases were washed with brine (50 ml) and dried over NaOH, filtered and evaporated. The residue was purified by Kugelrohr short path distillation at 160° C./20 mm Hg. The distillate was diluted with diethyl ether and 4.8M HCl solution in diethyl ether (3 ml) was added. The resulting precipitate was collected on a filter, washed with diethyl ether (35 ml) and dried in vacuo over NaOH to give 22 as a colorless solid. $^1$H-NMR (CDCl$_3$, TMS): 0.91 and 0.92 (total 12H, both s, 3',5'-CH$_3$); 1.28 (2H, s, 4'-CH$_2$); 1.89 and 1.93 (total 4H, both s, 2',6'-CH$_2$); 3.62 (2H, d, 7 Hz, CH$_2$N); 5.41 (1H, t, 7 Hz, —C=CH) and 8.3 ppm (3H, br s, NH$_3^+$).

EXAMPLE 11

2-(3,3,5,5-Tetramethylcyclohexylidene)propanamine hydrochloride (23)

a) 2-(3,3,5,5-Tetramethylcyclohexylidene)propionitrile (21).

Prepared according to the procedure for compound 20 (Example 10, a) using diethyl (1-cyanoethyl)phosphonate. Nitrile 21 obtained as a colorless oil with 41% yield. $^1$H-NMR: (CDCl$_3$, TMS): 0.96 and 1.00 (total 12H, both s, c-Hex-3,5-CH$_3$); 1.34 (2H, s, c-Hex-4-CH$_2$); 1.91 (3H, s, propionitrile-3-CH$_3$); 2.04 and 2.28 ppm (total 4H, both s, c-Hex-2,6-CH$_2$).

b) 2-(3,3,5,5-Tetramethylcyclohexylidene)propanamine hydrochloride (23).

Prepared from nitrile 21 according to the procedure for compound 22 (Example 10, b). Amine hydrochloride 23 obtained as a colorless solid. $^1$H-NMR: (CDCl$_3$, TMS): 0.92 and 0.93 (total 12H, both s, c-Hex-3,5-CH$_3$); 1.27 (2H, s, c-Hex-4-CH$_2$); 1.89 (3H, s, propanamine-3-CH$_3$); 1.99 and 2.01 (total 4H, both s, c-Hex-2,6-CH$_2$); 3.64 (2H, br s, propanamine-1-CH$_2$) and 8.40 ppm (3H, br s, NH$_3^+$).

Scheme: Example 12

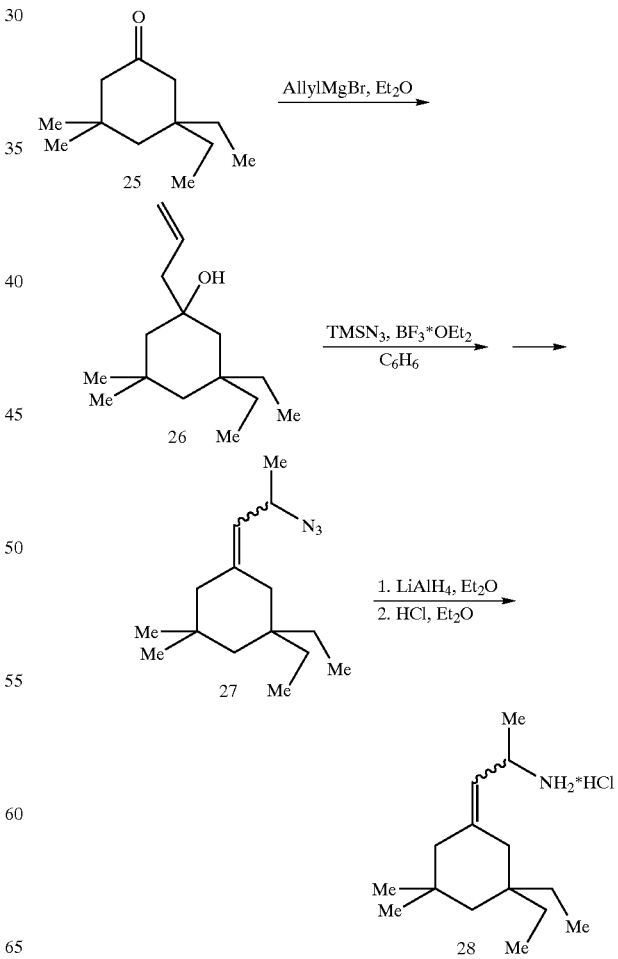

EXAMPLE 12

(E,Z)-1-(3,3-Diethyl-5,5-dimethylcyclohexylidene)-
2-propanamine hydrochloride (28)

a) 1-Allyl-3,3-diethyl-5,5-dimethylcyclohexanol (26).

To a stirred 1 M etheral solution of allylmagnesium bromide (20 ml, 20 mmol) was added dropwise a solution of 3,3-diethyl-5,5-dimethylcyclohexanone (25) (1.47 g, 8.06 mmol) in dry ether (5 ml). The mixture was stirred for 1 h at ambient temperature and boiled at reflux for 10 min. Then it was cooled with ice water and treated with saturated aqueous NH$_4$Cl (40 ml). The organic layer was separated and washed with water and brine. After drying over anhydrous MgSO$_4$, the solution was concentrated in vacuo. The residue was purified by column chromatography on silica gel (light petroleum ether). A fraction with Rf 0.7 (Hexane:EtOAc, 13:2) was collected. Evaporation of the solvent afforded 26 (1.35 g, 74%) as a colorless oil. $^1$H NMR (CDCl$_3$, TMS): 0.74 (6H, t, 7 Hz, 2CH$_3$ of ethyl); 0.88 (3H, s, 5-CH$_{3eq}$); 1.19 (3H, s, 5-CH$_{3ax}$); 0.80–2.05 (10H, m, 2,4,6-CH$_2$ and 2CH$_2$ of ethyl); 2.14 (2H, d, 7 Hz, CH$_2$C=); 4.95–5.30 (2H, m, =CH$_2$) and 5.65–6.20 ppm (1H, m, =CH).

b) (E,Z)-1-Methyl-2-(3,3-diethyl-5,5-dimethylcyclohexylidene)ethyl azide (27).

Prepared from cyclohexanol 26 according to the procedure for compounds 9 and 10 (Example 3, b). Azide 27 obtained as a colorless oil with 15% yield. $^1$H NMR (CDCl$_3$, TMS): 0.73 and 0.74 (total 6H, both t, 7 Hz, 2CH$_3$ethyl); 0.91, 0.94 and 0.97 (total 6H, all s, 5',5'-CH$_3$); 1.10–1.45 (4H, m, 2CH$_2$ ethyl); 1.22 (3H, d, 6.5 Hz, 1-CH$_3$); 1.26 (2H, s, 4'-CH$_2$); 1.89 (2H, s) and 1.97 (2H, m, 2,6-CH$_2$); 4.08–4.48 (1H, m, 1-CH) and 5.18 ppm (1H, dm, 9.5 Hz, =CH).

c) (E,Z)-1-(3,3-Diethyl-5,5-dimethylcyclohexylidene)-2-propanamine hydrochloride (28).

Prepared from azide 27 according to the procedure for compound 24 (Example 4). Amine hydrochloride 28 obtained as a colorless solid in 16% yield. $^1$H NMR (CDCl$_3$, TMS): 0.72 (6H, br t, 7 Hz, 2CH$_3$ ethyl), 0.90, 0.92 and 0.98 (total 6H, all s, 5',5'-CH$_3$); 1.25 (6H, m, 4'-CH$_2$ and 2CH$_2$ ethyl); 1.47 (3H, d, 6.5 Hz, 2-CH$_3$); 1.70–2.25 (2H, br AB q, 13 Hz, 2'-CH$_2$); 1.87 (2H, s, 6'-CH$_2$), 4.18 (1H, m, 2-CH); 5.34 (1H, br d, 9.5 Hz, =CH) and 8.38 ppm (3H, br s, NH$_3^+$).

Scheme: Example 13

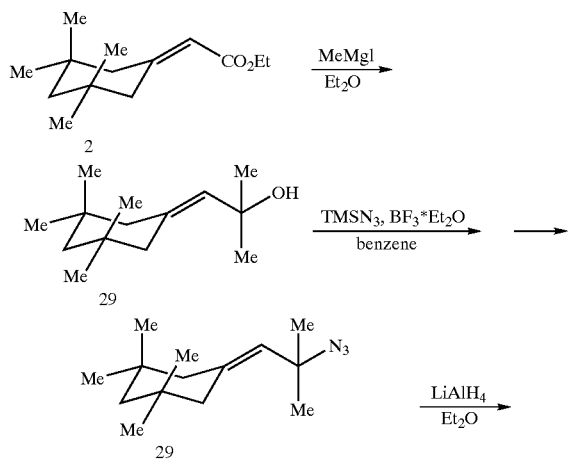

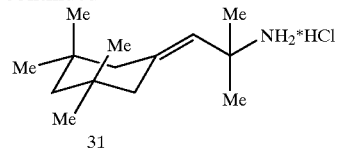

EXAMPLE 13

2-Methyl-1-(3,3,5,5-tetramethylcyclohexylidene)-2-propanamine hydrochloride (31)

a) 2-Methyl-1-(3,3,5,5-tetramethylcyclohexylidene)-2-propanol (29).

A solution of acetate 2 (2.14 g, 10 mmol) in diethyl ether (20 ml) was added to 1.6 M MeLi solution in diethyl ether (26 ml, 40 mmol), while cooling in an ice bath. The reaction mixture was stirred at room temperature for 1 h. It was then cooled in an ice bath and saturated aqueous NH$_4$Cl (20 ml) was added dropwise. The aqueous phase was extracted with diethyl ether (230 ml). The combined organic phases were washed with brine (30 ml), dried over MgSO$_4$, filtered and evaporated. The residue was purified by Kugelrohr short path distillation (100° C./4 mm Hg) to give 29 (1.86 g, 86%) as a colorless oil. $^1$H-NMR: (CDCl$_3$, TMS): 0.91 and 0.96 (total 12H, both s, c-Hex-3,5-CH$_3$); 1.25 (2H, s, c-Hex-4-CH$_2$); 1.38 (6H, s, —C(CH$_3$)$_2$O); 1.79 and 2.23 (both 2H, both s, c-Hex-2,6-CH$_2$) and 5.39 ppm (1H, s, =CH—).

b) 2-Azido-2-methyl-1-(3,3,5,5-tetramethylcyclohexylidene)propane (30).

BF$_3$Et$_2$O (0.3 ml, 2.4 mmol) was added to a solution of alcohol 29 (0.42 g, 2 mmol) and TMSN$_3$ (0.31 ml, 2.4 mmol) in benzene (4.5 ml) during 3 min, while cooling with an ice bath. The reaction mixture was stirred at 5–10° C. for 1 h and filtered through a short silica gel column. The solution was evaporated and the residue was purified by flash chromatography on silica gel (light petroleum ether) to give 30 (0.30 g, 64%) as a colorless oil. $^1$H-NMR (CDCl$_3$, TMS): 0.92 and 0.98 (total 12H, both s, c-Hex-3,5-CH$_3$); 1.27 (2H, s, c-Hex-4-CH$_2$); 1.40 (6H, s, —C(CH$_3$)$_2$N$_3$); 1.85 and 2.23 (both 2H, both s, c-Hex-2,6-CH$_2$) and 5.27 ppm (1H, s, =CH—).

c) 2-Methyl-1-(3,3,5,5-tetramethylcyclohexylidene)-2-propanamine hydrochloride (31).

Prepared from azide 30 by the same procedure as for amine 24 (Example 4). Amine hydrochloride 31 obtained as a colorless solid in 69% yield. $^1$H-NMR (CDCl$_3$, TMS): 0.91 and 0.98 (total 12H, both s, c-Hex-3,5-CH$_3$); 1.26 (2H, s, c-Hex-4-CH$_2$); 1.68 (6H, s, —C(CH$_3$)$_2$N); 1.84 and 2.10 (both 2H, both s, c-Hex-2,6-CH$_2$); 5.15 (1H, s, =CH—) and 8.5 ppm (3H, br s, NH$_3^+$).

Scheme: Examples 14 and 15

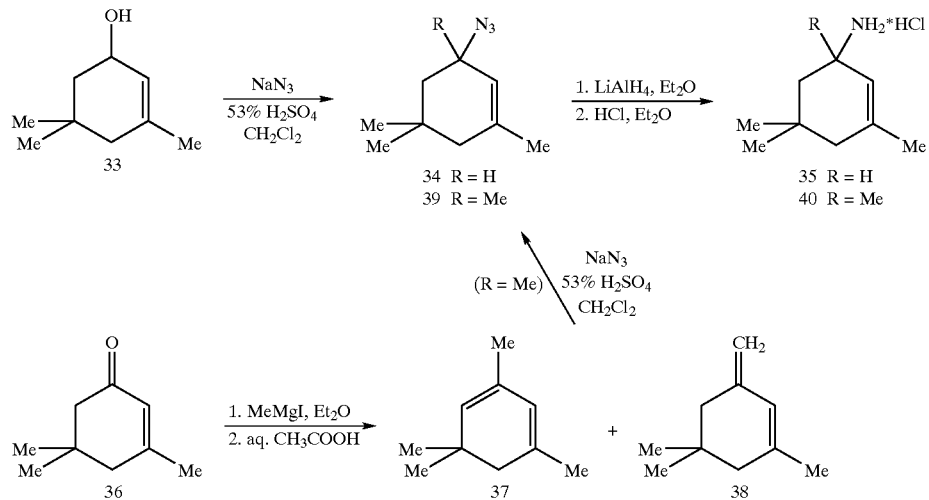

EXAMPLE 14

3,5,5-trimethyl-2-cyclohexen-1-amine hydrochloride (35)

a) 3-Azido-1,5,5-trimethyl-1-cyclohexene (34).

To a cooled (0° C.) suspension of sodium azide (0.81 g, 12.5 mmol) in $CH_2Cl_2$ (5 ml) was added dropwise 53% aqueous $H_2SO_4$ (8 ml). The mixture was stirred for 10 min, then a solution of 3,5,5-trimethyl-2-cyclohexanol (33) (0.70 g, 5 mmol) in $CH_2Cl_2$ (8 ml) was added. The mixture was stirred for 20 h, poured into ice water, neutralized with aqueous $NH_4OH$ and extracted with $CH_2Cl_2$. The extract was washed with brine and dried over $MgSO_4$. Filtration and evaporation of the solvent keeping the temperature below 25° C. gave an oil which was separated by column chromatography on silica gel (light petroleum ether). A fraction with Rf 0.8 (hexane) was collected. Evaporation of the solvent gave 34 as a colorless oil (0.365 g, 44%). $^1H$ NMR ($CDCl_3$, TMS): 0.89 and 1.01 (total 6H, both s, 5,5-$CH_3$); 1.34 (1H, m, c-4-CH); 1.55–1.95 (3H, m, 4-CH, 6-$CH_2$); 1.71 (3H, s, 1-$CH_3$); 3.90 (1H, m, 3-CH) and 5.39 ppm (1H, s, C=CH).

b) 3,5,5-trimethyl-2-cyclohexen-1-amine hydrochloride (35).

Prepared from azide 34 according to the procedure for compound 11 (Example 3, c). Amine hydrochloride 35 obtained as a colorless solid in 57% yield. $^1H$ NMR ($CDCl_3$, TMS): 0.89 and 1.03 (total 6H, both s, 5,5-$CH_3$); 1.25–2.15 (4H, m, 4,6-$CH_2$); 1.72 (3H, s, 3-$CH_3$); 3.88 (1H, m, 1-CH); 5.41 (1H, s, C=CH) and 8.40 ppm (3H, br s, $NH_3^+$).

EXAMPLE 15

1,3,5,5-Tetramethyl-2-cyclohexen-1-amine hydrochloride (40)

a) 1,3,5,5-Tetramethyl-1,3-cyclohexadiene (37) and 1,5,5-trimethyl-3-methylene-1-cyclohexene (38) mixture.

To a stirred 2 M etheral solution of methylmagnesium iodide (15 ml, 30 mmol) was added dropwise a solution of 3,5,5-trimethyl-2-cyclohexen-1-one (36) (1.38 g, 10 mmol) in dry ether (15 ml). The mixture was stirred for 1 h, cooled with ice water and carefully treated with 15% aqueous $CH_3COOH$ (15 ml). The mixture was stirred for an additional hour. The organic layer was separated and washed with water and saturated aqueous $NaHCO_3$. After drying over $MgSO_4$, the solution was concentrated in vacuo. The residue was purified by flash chromatography (light petroleum ether, Rf 0.95 (hexane)) to give a mixture of 37 and 38 (0.955 g, 70%) (7:10, based on GC) as an oil. $^1H$ NMR ($CDCl_3$, TMS). 0.89, 0.98 and 1.03 (total 10.2H, all s, 5,5-$CH_3$); 1.55–2.20 (total 12.6H, m, $CH_2C$= and $CH_3C$=); 4.69 (2H, dm, 4 Hz, =$CH_2$); 5.06 (0.7H, m, =CH); 5.50 (0.7H, sept, 1.5 Hz, =CH) and 5.92 ppm (1H, m, =CH).

b) 3-Azido-1,5,5,5-tetramethyl-1-cyclohexene (39).

Prepared from 37 and 38 mixture according to the procedure for compound 34 (Example 14, a). Azide 39 obtained as a colorless oil with 43% yield. $^1H$ NMR ($CDCl_3$, TMS): 0.93 and 0.99 (total 6H, both s, 5,5-$CH_3$); 1.31 (3H, s, 1-$CH_3$); 1.36 and 1.62 (total 2H, both d, 13 Hz, 4-$CH_2$); 1.72 (5H, s, 1-$CH_3$, 6-$CH_2$); 5.32 (1H, s, C=CH).

c) 1,3,5,5-Tetramethyl-2-cyclohexen-1-amine hydrochloride (40).

Prepared from azide 39 according to the procedure for compound 11 (Example 3, c). Amine hydrochloride 40 obtained as a colorless solid with 60% yield. $^1H$ NMR ($CDCl_3$, TMS): 0.96 and 1.07 (total 6H, both s, 5,5-$CH_3$); 1.56 (3H, s, 1-$CH_3$); 1.73 (3H, s, 3-$CH_3$); 1.60–2.05 (4H, m, 4,6-$CH_2$); 5.49 (1H, s, C=CH) and 8.27 ppm (3H, br s, $NH_3^+$).

Scheme: Example 16

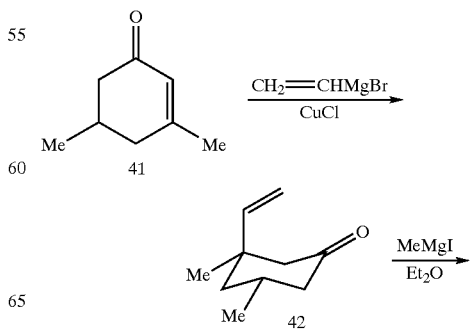

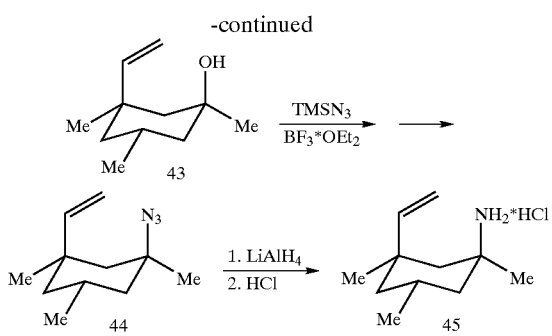

EXAMPLE 16

1,3, trans-5-trimethyl-cis-3-vinylcyclohexanamine hydrochloride (45)

a) 3,5-dimethyl-3-vinylcylohexanone (42).

A 1M solution of vinylmagnesium bromide in THF (90 ml, 90 mmol) was cooled in dry ice-acetone bath to −20° C. in an inert atmosphere and CuCl (4.45 g, 45 mmol) was added in one portion. The mixture was stirred for 30 min and a solution of 3,5-dimethyl-2-cyclohexen-1-one (41) (3.73 g, 30 mmol) in THF (40 ml) was added dropwise keeping the reaction temperature at −20° C. The cooling bath was removed and the reaction mixture was allowed to reach room temperature for 2 h. Saturated aqueous NH$_4$Cl (50 ml) was added thoroughly while cooling with ice bath. Hexane (150 ml) was then added and the aqueous layer was separated and extracted with hexane (2100 ml). The combined organic extracts were washed with 20% aqueous acetic acid (100 ml) and with saturated aqueous NaHCO$_3$ (3200 ml). The extract was dried over MgSO$_4$, filtered and evaporated. The crude product was purified by flash chromatography on silica gel (light petroleum ether-ethyl acetate, 20:1) to give 42 (2.4 g, 52%) as a colorless oil. $^1$H-NMR (CDCl$_3$, TMS): 0.99 (3H, d, 6 Hz, 5-CH$_3$); 1.11 (3H, s, 3-CH$_3$); 1.2–2.6 (7H, m, ring protons); 4.94 and 5.01 (total 2H, both d, 17 and 10.5 Hz, CH$_2$=) and 5.64 ppm (1H, dd, 17 and 11 Hz, =CH).

b) 1,3, trans-5-trimethyl-cis-3-vinylcyclohexanol (43).

A solution of ketone 42 (1 g, 6.6 mmol) in diethyl ether (10 ml) was added to 1.6M methyl lithium solution in diethyl ether (12 ml, 19.6 mmol) while cooling in an ice bath. The resulting mixture was stirred for 1 h at 0–5° C. and saturated aqueous NH$_4$Cl (10 ml) was added thoroughly. The aqueous layer was separated and extracted with diethyl ether (215 ml). The combined organic phases were washed with brine (20 ml) and dried over MgSO$_4$. The extract was filtered and evaporated. The crude product was purified by flash chromatography on silica gel (3% ethyl acetate in light petroleum ether). Cyclohexanol 43 (0.82 g, 74%) was obtained as a colorless oil that was used in the next step without characterization.

c) 1-Azido-1,3, trans-5-trimethyl-cis-3-vinylcyclohexane (44).

Prepared from cyclohexanol 43 according to the procedure for compound 9 (Example 3, b). Azide 44 obtained as a colorless oil with 17% yield. $^1$H-NMR (CDCl$_3$, TMS): 0.94 (3H, d, 6.5 Hz, 5-CH$_3$); 0.97 (3H, s, 3-CH$_3$); 1.27 (3H, s, 1-CH$_3$); 0.7–2.0 (7H, m, ring protons); 4.95 and 4.97 (total 2H, both d, 18 and 11 Hz, =CH$_2$) and 5.77 ppm (1H, dd, 18 and 11 Hz, =CH).

d) 1,3, trans-5-trimethyl-cis-3-vinylcyclohexanamine hydrochloride (45).

Prepared from azide 44 according to the procedure for compound 11 (Example 3, c). Amine hydrochloride 45 obtained as a colorless solid with 32% yield. $^1$H-NMR (CDCl$_3$, TMS): 0.92 (3H, d, 6.5 Hz, 5-CH$_3$); 0.96 (3H, s, 3-CH$_3$); 1.45 (3H, s, 1-CH$_3$); 0.8–2.1 (9H, m, 2,4,6-CH$_2$, 5-CH and H$_2$O); 4.94 and 4.97 (2H, both d, 18 and 11 Hz, =CH$_2$); 5.76 (1H, dd, 18 and 11 Hz, =CH) and 8.26 ppm (3H, br s, NH$_3^+$).

Scheme: Example 17

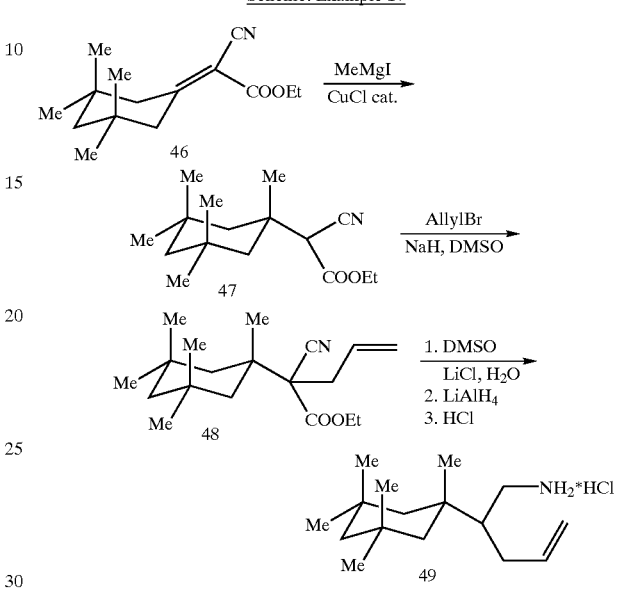

EXAMPLE 17

2-(1,3,3,5,5-Pentamethylcyclohexyl)-4-pentenylamine hydrochloride (49)

a) Ethyl 2-cyano-2-(1,3,3,5,5-pentamethylcyclohexyl) acetate (47).

Copper (I) chloride (0.05 g, 0.5 mmol) was added to a cooled (−10° C.) in argon atmosphere 1M methylmagnesium iodide in ethyl ether (15 ml, 15 mmol) and stirred for 5 min. Then a solution of acetate 46 (2.5 g, 10 mmol) in THF (25 ml) was added dropwise within 20 min, keeping the temperature below 0° C. The mixture was stirred for 1 h, quenched with saturated aqueous NH$_4$Cl, and extracted with diethyl ether The extract was washed with brine, dried over anhydrous MgSO$_4$, filtered and evaporated. The residue was purified by flash chromatography on silica gel (light petroleum ether-ethyl acetate, 20:1) to give 47 (1.5 g, 56.5%) as a colorless oil. $^1$H NMR (CDCl$_3$, TMS): 1.01, 1.07 and 1.09 (total 12H, s, 3',5'-CH$_3$); 1.00–1.85 (6H, m, ring CH); 1.30 (3H, s, 1'-CH$_3$); 1.33 (3H, t, 7 Hz, CH$_3$-ethyl); 3.44 (1H, s, 2-CH) and 4.27 ppm (2H, q, 7 Hz, OCH$_2$).

b) Ethyl 2-cyano-2-(1,3,3,5,5-pentamethylcyclohexyl)-4-pentenoate (48)

To a solution of cyanoacetate 47 (1.25 g, 4.71 mmol) in anhydrous DMSO (10 ml) was added sodium hydride (0.284 g, 7.09 mmol; 60% mineral oil dispersion). The mixture was stirred for 30 min at 50° C., and cooled to 20° C. To this was added allylbromide (0.86 g, 7.1 mmol) and the mixture was stirred for 3 h at room temperature, then for 30 min at 50° C. The mixture was cooled, treated with water and extracted with diethyl ether. The extract was washed with water and with brine, dried over anhydrous MgSO$_4$, filtered and evaporated. The residue was purified by flash chromatography on silica gel (light petroleum ether-ethyl acetate, 20:1) to give 48 (0.92 g, 63.7%) as a colorless oil. $^1$H NMR (CDCl$_3$, TMS): 0.98 (6H, s, 3',5'-CH$_{3eq}$); 1.11 (6H, s, 3',5'-CH$_{3ax}$); 1.00–1.85 (6H, m, ring CH); 1.31 (3H, t, 7 Hz, CH$_3$-ethyl); 1.33 (3H, s, 1'-CH$_3$); 2.42 and 2.86 (total 2H, both dd, 13 and 7 Hz, 3-CH$_2$); 4.02 (2H, q, 7 Hz, OCH$_2$); 5.05–5.37 (2H, m, =CH$_2$) and 5.55–6.05 ppm (1H, m, =CH).

c) 2-(1,3,3,5,5-Pentamethylcyclohexyl)-4-pentenylamine hydrochloride (49)

To a solution of ester 48 (0.9 g, 2.95 mmol) in DMSO (10 ml) was added water (0.53 ml, 2.95 mmol) and lithium chloride (0.25 g, 5.9 mmol). The mixture was stirred for 3 h at 175–180° C., then it was cooled and water (30 ml) was added. The mixture was extracted with diethyl ether. The extract was washed with water and with brine, dried over anhydrous MgSO$_4$, filtered and concentrated to 10 ml volume. The solution obtained was added dropwise to a suspension of lithium aluminum hydride (0.25 g, 6.6 mmol) in diethyl ether (15 ml) and stirred at reflux for 3 h. The mixture was cooled and treated with 20% aqueous NaOH, and extracted with diethyl ether. The extract was washed with brine, dried over NaOH, filtered and treated with anhydrous HCl solution in diethyl ether. After evaporation of the solvent, the residue was purified by chromatography on silica gel (chloroform-methanol, 20:1) to give 49 (0.245 g, 31%) as a colorless solid. $^1$H NMR (DMSO-D$_6$, TMS): 0.92, 0,96 and 1.04 (total 15H, all s, 3',5'-CH$_3$ and 1'-CH$_3$), 1.00–1.65 (total 6H, m, ring-CH$_2$); 1.85–2.40 (3H, m, 3-CH$_2$, 4-CH); 2.60–3.10 (2H, m, CH$_2$N); 4.90–5.25 (2H, m, =CH$_2$); 5.62–6.10 (1H, m, =CH) and 7.92 ppm (3H, br s, NH$_3^+$).

Pharmaceutical Compositions

The active ingredients of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing twenty (20) to one hundred (100) milligrams of active ingredient or, more broadly, ten (10) to two hundred fifty (250) milligrams per tablet, are accordingly suitable representative unit dosage forms.

Method of Treating

Due to their high degree of activity and their low toxicity, together presenting a most favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Suitable dosage ranges are 1–1000 milligrams daily, preferably 10–500 milligrams daily, and especially 50–500 milligrams daily, depending as usual upon the exact mode of administration, form in which administered, the indication toward which the administration is directed, the subject involved and the body weight of the subject involved, and the preference and experience of the physician or veterinarian in charge.

EXAMPLES OF REPRESENTATIVE PHARMACEUTICAL COMPOSITIONS

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration which contain the active ingredient may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

The following examples are again given by way of illustration only and are not to be construed as limiting.

Example 1

Tablet Formulation
A suitable formulation for a tablet containing 10 milligrams of active ingredient is as follows:

|  | Mg. |
|---|---|
| Active Ingredient | 10 |
| Lactose | 63 |
| Microcrystalline Cellulose | 21 |
| Talcum | 4 |
| Magnesium stearate | 1 |
| Colloidal silicon dioxide | 1 |

Example 2

Tablet Formulation
Another suitable formulation for a tablet containing 100 mg is as follows:

|  | Mg. |
|---|---|
| Active Ingredient | 100 |
| Potato starch | 20 |
| Polyvinylpyrrolidone | 10 |
| Film coated and colored. | |

-continued

Tablet Formulation
Another suitable formulation for a tablet containing 100 mg is as follows:

| | Mg. |
|---|---|
| The film coating material consists of: | |
| Lactose | 100 |
| Microcryst. Cellulose | 80 |
| Gelatin | 10 |
| Polyvinylpyrrolidone, crosslinked | 10 |
| Talcum | 10 |
| Magnesium stearate | 2 |
| Colloidal silicon dioxide | 3 |
| Color pigments | 5 |

Example 3

Capsule Formulation
A suitable formulation for a capsule containing 50 milligrams of active ingredient is as follows:

| | Mg. |
|---|---|
| Active Ingredient | 50 |
| Corn starch | 20 |
| Dibasic calcium phosphate | 50 |
| Talcum | 2 |
| Colloidal silicon dioxide | 2 | filled in a gelatin capsule.

Example 4

Solution for injection
A suitable formulation for an injectable solution containing one percent of active ingredient is as follows:

| | |
|---|---|
| Active Ingredient mg | 12 |
| Sodium chloride mg | 8 |
| Sterile water to make ml | 1 |

Example 5

Liquid oral formulation
A suitable formulation for 1 liter of a liquid mixture containing 2 milligrams of active ingredient in one milliliter of the mixture is as follows:

| | G. |
|---|---|
| Active Ingredient | 2 |
| Saccharose | 250 |
| Glucose | 300 |
| Sorbitol | 150 |
| Orange flavor | 10 |
| Sunset yellow. | |
| Purified water to make a total of 1000 ml. | |

Example 6

Liquid oral formulation
Another suitable formulation for 1 liter of a liquid mixture containing 20 milligrams of active ingredient in one milliliter of the mixture is as follows:

| | G. |
|---|---|
| Active Ingredient | 20.00 |
| Tragacanth | 7.00 |
| Glycerol | 50.00 |
| Saccharose | 400.00 |
| Methylparaben | 0.50 |
| Propylparaben | 0.05 |
| Black currant-flavor | 10.00 |
| Soluble Red color | 0.02 |
| Purified water to make a total of 1000 ml. | |

Example 7

Liquid oral formulation
Another suitable formulation for 1 liter of a liquid mixture containing 2 milligrams of active ingredient in one milliliter of the mixture is as follows:

| | G. |
|---|---|
| Active Ingredient | 2 |
| Saccharose | 400 |
| Bitter orange peel tincture | 20 |
| Sweet orange peel tincture | 15 |
| Purified water to make a total of 1000 ml. | |

Example 8

Aerosol formulation
180 g aerosol solution contain:

| | G. |
|---|---|
| Active Ingredient | 10 |
| Oleic acid | 5 |
| Ethanol | 81 |
| Purified Water | 9 |
| Tetrafluoroethane | 75 |

Example 9

TDS formulation
100 g solution contain:

| | G. |
|---|---|
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

Example 10

| Nanoparticle formulation 10 g of polybutylcyanoacrylate nanoparticles contain: | |
|---|---|
| | G. |
| Active Ingredient | 1.00 |
| Poloxamer | 0.10 |
| Butylcyanoacrylate | 8.75 |
| Mannitol | 0.10 |
| Sodium chloride | 0.05 |

Polybutylcyanoacrylate nanoparticles are prepared by emulsion polymerization in a water/0.1 N HCl/ethanol mixture as polymerizsation medium. The nanoparticles in the suspension are finally lyophilized under vacuum.

Pharmacology—Summary

The active principles of the present invention, and pharmaceutical compositions thereof and method of treating therewith, are characterized by unique advantageous and unexpected properties, rendering the "subject matter as a whole", as claimed herein, unobvious. The compounds and pharmaceutical compositions thereof have exhibited, in standard accepted reliable test procedures, the following valuable properties and characteristics:

They are systemically-active, uncompetitive NMDA receptor antagonists with rapid blocking/unblocking kinetics and strong voltage dependency and are, accordingly, of utility in the treatment, elimination, palliation, alleviation, and amelioration of responsive conditions, by application or administration to the living animal host for the treatment of a wide range of CNS disorders which involve disturbances of glutamatergic transmission.

These compounds are also systemically-active, non-competitive $5HT_3$ and neuronal nicotinic receptor antagonists and are, accordingly, of utility in the treatment, elimination, palliation, alleviation, and amelioration of responsive conditions, by application or administration to the living animal host for the treatment of a wide range of CNS disorders which involve disturbances of serotonin or nicotinic transmission.

Methods
Receptor Binding Studies

Male Sprague-Dawley rats (200–250 g) were decapitated and their brains were removed rapidly. The cortex was dissected and homogenized in 20 volumes of ice-cold 0.32 M sucrose using a glass-Teflon homogenizer. The homogenate was centrifuged at 1000×g for 10 min. The pellet was discarded and the supernatant centrifuged at 20,000×g for 20 min. The resulting pellet was re-suspended in 20 volumes of distilled water and centrifuged for 20 min at 8000×g. Then the supernatant and the buffy coat were centrifuged at 48,000×g for 20 min in the presence of 50 mM Tris-HCl, pH 8.0. The pellet was then re-suspended and centrifuged two to three more times at 48,000×g for 20 min in the presence of 50 mM Tris-HCl, pH 8.0. All centrifugation steps were carried out at 4° C. After resuspension in 5 volumes of 50 mM Tris-HCl, pH 8.0 the membrane suspension was frozen rapidly at −80° C.

On the day of assay the membranes were thawed and washed four times by resuspension in 50 mM Tris-HCl, pH 8.0 and centrifugation at 48,000×g for 20 min. and finally re-suspended in 50 mM Tris-HCl, pH 7.4. The amount of protein in the final membrane preparation (250–500 µg/ml) was determined according to the method of Lowry et al. (1951). Incubations were started by adding [$^3$H]—(+)-MK-801 (23.9 Ci/mmol, 5 nM, Dupont NEN) to vials with glycine (10 µM), glutamate (10 µM), and 125–250 µg protein (total volume 0.5 ml) and various concentrations of the agents tested (10 concentrations in duplicates). The incubations were continued at room temperature for 120 min (equilibrium was achieved under the conditions used). Non-specific binding was defined by the addition of unlabeled (+)-MK-801 (10 µM). Incubations were terminated using a Millipore filter system. The samples were rinsed twice with 4 ml of ice cold assay buffer over glass fibre filters (Schleicher & Schuell) under a constant vacuum. Following separation and rinse the filters were placed into scintillation liquid (5 ml; Ultima Gold) and radioactivity retained on the filters was determined with a conventional liquid scintillation counter (Hewlett Packard, Liquid Scintillation Analyser). The Kd of [$^3$H]-(+)-MK-801 of 4.6 nM was determined by Scatchard analysis and used according to the Cheng Prussoff relationship to calculate the affinity of displacers as Kd values. Most antagonists were tested in 3 to 7 separate experiments.

NMDA and Neuronal Nicotinic Receptor Subtype Expression in *Xenopus* Oocytes

Mature female *Xenopus laevis* were anaesthetized in 0.2% Tricaine on ice for 15 min prior to surgery. Oocytes were removed and incubated in 2 mg/ml collagenase (type II) in $Ca^{2+}$-free oocyte Ringer solution (82.5 mM NaCl, 2 mM KCl, 2 mM $MgCl_2$, 5 mM HEPES, pH 7.5) for 30 min. at room temperature and washed thoroughly with OR-2 (100 mM NaCl, 2 mM KCl, 1 mM $MgCl_2$, 2 mM $CaCl_2$, 5 mM HEPES, pH 7.5). The remaining follicle cell layer was removed manually with fine forceps and the oocytes were kept in OR-2. The RNA was dissolved in DEPC-treated, sterile distilled water. RNA for the NMDA NR1a subunit was mixed 1:1 with RNA for the NR2A subunit. Likewise neuronal nicotinic α4 RNA was mixed 1:1 with RNA for the β2 subunit. Fifty to 100 nanoliters of each RNA mixture were injected in the oocyte's cytoplasm using a Nanoliter Injector (World Precision Instruments). The oocytes were incubated at 19° C. in OR-2 for the following 3 to 6 days.

The electrophysiological responses were obtained using the standard two-electrode voltage-clamp method (GeneClamp 500 amplifier), 2–6 days after injection. The electrodes had a resistance between 0.2 and 0.4 MΩ and were filled with 3M KCl. Recordings were made in a custom made chamber with 2 to 3 second exchange times. The bath solution was prepared $Ca^{2+}$-free, to avoid $Ca^{2+}$-induced $Cl^-$ currents (100 mM NaCl, 2 mM KCl, 5 mM HEPES, 2 mM $BaCl_2$, pH 7.35). NMDA receptors were activated by the manual co-application of 1 mM Glutamate and 10 µM Glycine for 30–40 secs every 2 to 3 mins to oocytes clamped at −70 mV. Neuronal nicotinic receptors were activated by application of 100 µM acetylcholine for 20–30 secs every 2 to 3 mins to oocytes clamped at −70 mV. After obtaining stable control responses, full concentration-response curves with antagonists were obtained by preincubating 6–7 different concentrations at log 3 intervals.

Only results from stable cells were accepted for inclusion in the final analysis i.e. showing at least 50% recovery of responses to NMDA following removal of the antagonist tested. Despite this, recovery from drug actions wasn't always 100% because of minor rundown or runup in some cells. When present, this was always compensated by basing the % antagonism at each concentration on both control and recovery and assuming a linear time course for this rundown. All antagonists were assessed at steady-state blockade with 6 to 7 concentrations on at least 4 cells. Equilibrium blockade was achieved within 1 to 3 agonist applications, depending on antagonist concentration.

Kinetic experiments were performed by applying various concentrations of unsaturated amino-alkyl-cyclohexanes (normally 5 in a log 3 dosing regime) for 10–20 seconds in the continuous presence of glutamate (100 $\mu$M and glycine 10 $\mu$M) for 90–180 seconds in *Xenopus oocytes* expressing NR1a/2A receptors. The perfusion system used for these experiments was a modified oocyte carousel system which allows rapid wash in and wash out of agonist and antagonist with change times less than one second. Exponential fits were made using the program TIDA for windows and most responses were well fitted by a single exponential. This same system was used to access the voltage-dependency of blockade, but the bath solution contained flufenamic acid (100 $\mu$M) to block endogenous voltage-activated and $Ca^{2+}$ activated $Cl^-$ currents. Also, $Ba^{2+}$ (2 mM) was replaced by low concentrations of $Ca^{2+}$ (0.2 mM). Following equilibrium blockade by higher concentrations of antagonist (normally around 10 times the $IC_{50}$), five ramps were driven from −70 mV to +30 mV over two seconds. Similar ramps were driven in bath solutions and for glutamate without antagonist, both before antagonist application and following recovery of responses. The leak currents in the absence of glutamate were substrated from the glutamate and glutamate plus antagonist curves. Voltage-dependency was then determined by comparing the glutamate and glutamate plus antagonist curves.

Patch Clamp for NMDA and Nicotine

Hippocampi were obtained from rat embryos (E20 to E21) and were then transferred to calcium and magnesium free Hank's buffered salt solution (Gibco) on ice. Cells were mechanically dissociated in 0.05% DNAase/0.3% ovomucoid (Sigma) following an 8 minute pre-incubation with 0.66% trypsin/0.1% DNAase (Sigma). The dissociated cells were then centrifuged at 18×g for 10 minutes, re-suspended in minimum essential medium (Gibco) and plated at a density of 150,000 cells $cm^{-2}$ onto poly-L-lysine (Sigma)-precoated plastic petri dishes (Falcon). The cells were nourished with $NaHCO_3$/HEPES-buffered minimum essential medium supplemented with 5% fetal calf serum and 5% horse serum (Gibco) and incubated at 37C with 5% $CO_2$ at 95% humidity. The medium was exchanged completely following inhibition of further glial mitosis with cytosine-D-arabinofuranoside (20M Sigma) after about 7 days in vitro. Thereafter the medium was exchanged partially twice weekly.

Patch clamp recordings were made from these neurones with polished glass electrodes (4–6 m) in the whole cell mode at room temperature (20–22C) with the aid of an EPC-7 amplifier (List). Test substances were applied by switching channels of a custom-made fast superfusion system with a common outflow (10–20 ms exchange times). The contents of the intracellular solution were as follows (mM): CsCl (120), TEACl (20), EGTA (10), $MgCl_2$(1), $CaCl_2$(0.2), glucose (10), ATP (2), cAMP (0.25); pH was adjusted to 7.3 with CsOH or HCl. The extracellular solutions had the following basic composition (mM): NaCl (140), KCl (3), $CaCl_2$ (0.2), glucose (10), HEPES (10), sucrose (4.5), tetrodotoxin (TTX $3*10^{-4}$). Glycine (1M) was present in all solutions: a concentration sufficient to cause around 80–85% activation of $glycine_B$ receptors. Only results from stable cells were accepted for inclusion in the final analysis, i.e., following recovery of responses to NMDA by at least 75% of their depression by the antagonists tested.

Patch Clamp for 5-HT3

N1E-115 cells were purchased from the European collection of cell cultures (ECACC, Salisbury, UK) and stored at −80° C. until further use. The cells were plated at a density of 100,000 cells $cm^{-2}$ onto plastic Petri dishes (Falcon) and were nourished with $NaHCO_3$/HEPES-buffered minimum essential medium supplemented (MEM) with 15% fetal calf serum (Gibco) and incubated at 37° C. with 5%$CO_2$ at 95% humidity. The medium was exchanged completely daily. Once every three days, cells were reseeded onto fresh Petri dishes following treatment with trypsin-EDTA (1% in PBS), resuspension in MEM and centrifugation at 1000 rpm for four minutes.

Patch clamp recordings at −70 mV were made from lifted cells, 2–3 days following seeding with polished glass electrodes (2–6M$\Omega$) in the whole cell mode at room temperature (20–22° C.) with an EPC-7 amplifier (List). The contents of the intracellular solution were as follows (mM): CsCl (130), HEPES (10), EGTA (10), $MgCl_2$ (2), $CaCl_2$ (2), K-ATP (2), Tris-GTP (0.2), D-glucose (10); pH was adjusted to 7.3 with CsOH or HCl. The extracellular solutions had the following basic composition (mM): NaCl (124), KCl (2.8), HEPES (10), pH 7.3 adjusted with NaOH or HCl.

After the whole-cell configuration was established, the cells were lifted from the glass substrate and serotonin (10 $\mu$M), memantine and unsaturated amino-alkyl-cyclohexane derivatives were applied at various concentrations using a fast superfusion device. A piezo translator-driven double-barrelled application pipette was used to expose the lifted cell either to serotonin-free or serotonin-containing solution. A two second serotonin pulse was delivered every 60 seconds. The putative antagonists were dissolved in aquabidest and diluted with bath solution to the desired concentration. Only results from stable cells were accepted for inclusion in the final analysis, i.e., showing at least 50% recovery of responses to serotonin following removal of compounds. Despite this, recovery from drug actions wasn't always 100% because of rundown in some cells (<=10% over 10 minutes). When present, this was always compensated by basing the percent antagonism at each concentration on both control and recovery and assuming a linear time course for this rundown. All antagonists were assessed at steady-state blockade with 3 to 6 concentrations on at least five cells. Equilibrium blockade was achieved within 2 to 5 agonist applications, depending on antagonist concentration.

In vivo

Anticonvulsive Activity

NMR female mice (18–28 g) housed 5 per cage were used for the maximal electroshock (MES) and motor impairment tests. All animals were kept with water and food ad libitum under a 12 hour light-dark cycle (light on at 6 a.m.) and at a controlled temperature (20±0.5C). All experiments were performed between 10 a.m. and 5 p.m. Tested agents were injected 30 min. i.p. before the induction of convulsions if not stated otherwise (see below). All compounds were dissolved in 0.9% saline.

The MES test was performed together with tests for myorelaxant action (traction reflex) and motor coordination (rotarod). For the traction reflex test mice were placed with their forepaws on a horizontal rod and were required to place all 4 paws on the wire within 10 seconds. To test ataxia (motor coordination) mice were placed on an accelerating rotarod and were required to remain on the rod for 1 minute. Only mice not achieving the criteria in all three repetitions of each test were considered to exhibit myorelaxation or ataxia respectively. These tests were followed by MES (100 Hz, 0.5 second shock duration, 50 mA shock intensity, 0.9 ms impulse duration, Ugo Basile) applied through corneal electrodes. The presence of tonic convulsions was scored (tonic extension of hind paws with minimum angle to the body of 90). The aim was to obtain $ED_{50}s$ for all parameters scored (anticonvulsive activity and motor side effects) with use of the Litchfield Wilcoxon test for quantal dose responses. Division of the $ED_{50}$ for side effects (ataxia or myorelaxation) by the $ED_{50}$ for antagonism of electroshock convulsions was used as a therapeutic index (TI).

Statistical Analysis $IC_{50}s$ in patch clamp and binding studies were calculated according to the four parameter logistic equation using the Grafit computer program (Erithacus Software, England). Ki value for binding studies were then determined according to Cheng and Prusoff. Binding values presented are means±SEM of 3–5 determinations (each performed in duplicate).

4–7 doses of antagonists were tested in each of the in vivo tests (5–8 animals per dose) to allow calculation of graded $ED_{50}s$ according to probit analysis (Litchfield and Wilcoxon) with correction for 0% to 100% effects. $ED_{50}s$ are presented with 95% confidence limits (Cl). Pearson product moment correlation analysis (Sigma Stat, Jandel Scientific) was used to compare in vitro potencies and in vivo anticonvulsant activity.

Results

MRZ Numbers

MRZ numbers are used to represent chemical names. The MRZ numbers and their respective chemical names are shown in "MRZ LIST".

MRZ LIST

| MRZ | Chemical Name |
|---|---|
| 2/657 | 1-amino-2,4,4,6,6-pentamethyl-cyclohex-2-en Hydrochloride |
| 2/749 | 1-(1-Aminoethyl)-3,3,5,5-tetramethylcyclohex-1-ene |
| 2/759 | 1-Ethenyl-3,3,5,5-tetramethylcyclohexylamine |
| 2/1005 | 1-Amino-3,3,5,5-Tetramethyl-1-cyclohexene |
| 2/1021 | 2-(3,3,5,5-Tetramethylcyclohexylidene)ethanamine |
| 2/1023 | 1-Amino-3,3,5-trimethyl-2-cyclohexene |
| 2002 | 1,3,5,5-Tetramethyl-2-cyclohexen-1-amine |
| 2005 | 1-Allyl-3,3,5,5-tetramethylcyclohexanamine |
| 2006 | 1-(3,3,5,5-Tetramethylcyclohexylidene)-2-propanamine |
| 2008 | 1-(3,3-Diethyl-5,5-dimethylcyclohexylidene)-2-propanamine |
| 2009 | cis-3-Vinyl-1,3,trans-5-trimethylcyclohexylamine |
| 2010 | 2-Methyl-1-(3,3,5,5-tetramethyl-1-cyclohexen-1-yl)-2-propanamine |
| 2013 | 1-(1-Allyl-3,3,5,5-tetramethylcyclohexyl)piperidine |
| 2014 | 2-(1-Vinyl-3,3,5,5-tetramethylcyclohexyl-1)ethylamine |
| 2015 | 1-[3,3,5,5-Tetramethyl-1-(3-methyl-2-butenyl)cyclohexyl]piperidine |
| 2016 | 1-[3,3,5,5-Tetramethyl-1-(2-propynyl)cyclohexyl]piperidine |
| 2017 | 2-(1,3,3,5,5-Pentamethylcyclohexyl)-4-pentenylamine |
| 2018 | 3-(3,3,5,5-Tetramethylcyclohexylidene)propanamine |
| 2019 | 2-Methyl-1-(3,3,5,5-tetramethylcyclohexylidene)-2-propanamine |
| 2020 | 2-(3,3,5,5-Tetramethylcyclohexylidene)propanamine |
| 2021 | N-Methyl-1-ethenyl-3,3,5,5-tetramethylcyclohexylamine |
| 2026 | N-Allyl-1,3,3,5,5-pentamethylcyclohexanamine |

Binding MK-80

All compounds displaced $[^3H]$-(+)-MK-801 with Ki values between 1 and 83 $\mu M$ (see Table 1).

TABLE 1

| MRZ | Group | $[^3H]$MK-801 Ki | SEM | n | NMDA $IC_{50}$ ($\mu M$) | SEM | N |
|---|---|---|---|---|---|---|---|
| 2/657 | Ethylene Ring | 13.43 | 1.15 | 3 | | | |
| 2/749 | Ethylene Ring | 10.76 | 1.49 | 3 | | | |
| 759 | Ethylene | 1.18 | 0.20 | 6 | 3.28 | 0.60 | 6 |
| 2/1005 | Ethylene Ring | 13.63 | 1.43 | 4 | | | |
| 2/1021 | Ethylene | 2.15 | 0.32 | 6 | 0.33 | 0.05 | 6 |
| 1023 | Ethylene Ring | 49.60 | 8.09 | 6 | | | |
| 2000 | Neramexane Sulphate | 1.68 | 0.00 | 3 | | | |
| 2002 | Ethylene Ring | 5.70 | 0.48 | 3 | | | |
| 2005 | Ethylene | 9.35 | 0.12 | 3 | 12.60 | 5.68 | 6 |
| 2006 | Ethylene | 10.06 | 0.40 | 3 | | | |
| 2008 | Ethylene | 8.07 | 0.57 | 3 | 2.74 | 0.22 | 6 |
| 2009 | Ethylene | 22.32 | 0.88 | 3 | 58.17 | 8.87 | 6 |
| 2013 | Ethylene | 49.21 | 11.73 | 3 | | | |
| 2014 | Ethylene | 3.12 | 0.67 | 3 | 0.10 | 0.01 | 6 |
| 2015 | Ethylene | 83.04 | 30.98 | 3 | | | |
| 2016 | Ethylene | 42.22 | 13.60 | 3 | 71.17 | 14.66 | 6 |
| 2017 | Ethylene | 6.79 | 0.51 | 3 | 1.19 | 0.16 | 6 |
| 2018 | Ethylene | 20.18 | 2.80 | 3 | 37.06 | 13.37 | 6 |
| 2019 | Ethylene | 73.06 | 8.67 | 3 | | | |
| 2020 | Ethylene | 7.45 | 0.69 | 3 | | | |
| 2021 | Ethylene | 6.54 | 0.72 | 3 | 12.73 | 0.50 | 6 |
| 2010 | Ethylene Ring | 44.88 | 13.91 | 3 | | | |
| 2026 | Ethylene | | | | 29.56 | 1.64 | 6 |

The results for representative compounds are reported in FIG. 1.

NMDA Receptor Subtype Expression in *Xenopus* Oocytes

NMDA receptor blockade by MRZ 2/759 was determined by applying various concentrations (0.1 to 100 $\mu$M in a log 3 dosing regime) for 10 seconds in the continuous presence of glutamate (100 $\mu$M) and glycine 10 $\mu$M) at −70 mV for 100 seconds in *Xenopus* oocytes expressing NR1a/2A receptors (FIG. 2, left). The potency of MRZ 2/759 (IC$_{50}$=1.99 $\mu$M, Hill 0.75) was determined by plotting percent blockade against antagonist concentration and then fitting the curve according to the logistic equation (FIG. 2, right).

Patch Clamp

Steady-state inward current responses of freshly dissociated hippocampal neurones to NMDA (200M with glycine 1M at −70 mV) were antagonized by MRZ 2/759. Peak and steady-state currents were affected to a similar degree making it unlikely that its effects were mediated at the glycine$_B$ site. Strong support for the uncompetitive nature of this antagonism was provided by the clear use- and voltage-dependency of its blockade. See FIG. 3.

Invivo
Anti-Convulsive Activity

MES and Myorelaxant action results are presented in Table 2.

according to the present invention, as well as novel pharmaceutical compositions thereof and methods of preparation thereof and of treating therewith, all possessed of the foregoing more specifically-enumerated characteristics and advantages.

The high order of activity o the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

CONCLUSIONS

The instant unsaturated 1-amino-alkylcyclohexanes represent a novel class of systemically-active, uncompetitive NMDA receptor antagonists with rapid blocking/unblocking kinetics and strong voltage-dependency. In view of their moderate potency and associated rapid kinetics, they will be useful therapeutics in a wide range of CNS disorders which involve disturbances of glutamatergic transmission.

These compounds accordingly find application in the treatment of the following disorders of a living animal body,

TABLE 2

| MRZ | MES ED50 | MES CL | Myorelaxation ED50 | Myorelaxation Cl | Ataxia ED50 | Ataxia Cl | TI Myorelaxation | TI Ataxia |
|---|---|---|---|---|---|---|---|---|
| 2/657 | >30 | | >30 | | >30 | | | |
| 2/749 | 26.58 | 20.7–34.1 | 38.64 | 28.6–52.1 | 37.14 | 30.0–46.0 | 1.5 | 1.4 |
| 2/759 | 14.84 | 9.6–23.1 | 12.76 | 10.3–15.9 | 15.00 | 11.4–19.8 | 0.9 | 1.0 |
| 2/1005 | 20.48 | 9.6–43.9 | 35.66 | 26.1–48.7 | 26.83 | 16.1–44.8 | 1.7 | 1.3 |
| 2/1021 | 29.46 | 17.8–48.9 | 16.50 | 10.9–25.0 | 23.09 | 15.2–35.0 | 0.6 | 0.8 |
| 2/1023 | >50 | | >50 | | >50 | | | |
| 2002 | 26.14 | 21.0–32.5 | 33.96 | 27.1–42.6 | 52.98 | 27.8–100.8 | 1.3 | 2.0 |
| 2005 | 37.34 | 33.9–41.1 | 39.75 | 32.6–48.4 | 49.34 | 37.2–65.5 | 1.1 | 1.3 |
| 2006 | 57.02 | 31.4–103.4 | 44.62 | 39.4–50.5 | 40.88 | 31.4–58.9 | 0.8 | 0.7 |
| 2008 | | | | | | | | |
| 2009 | >50 | | >50 | | >50 | | | |
| 2010 | >50 | | >50 | | >50 | | | |
| 2013 | >50 | | >50 | | >50 | | | |
| 2014 | 47.82 | 21.5–106.5 | 13.95 | 6.3–31.1 | 25.83 | 18.3–36.4 | 0.3 | 0.5 |
| 2015 | >50 | | >50 | | >50 | | | |
| 2016 | >50 | | >50 | | >50 | | | |
| 2017 | 36.88 | 29.1–46.7 | 35.63 | 30.0–42.3 | 33.72 | 25.0–45.4 | 1.0 | 0.9 |
| 2018 | 78.54 | 35.0–176.3 | 29.43 | 23.4–37.0 | 26.70 | 19.2–37.0 | 0.4 | 0.3 |
| 2019 | >50 | | >50 | | >50 | | | |
| 2020 | 26.06 | 20.4–33.3 | 34.46 | 29.1–40.8 | 27.57 | 18.7–40.7 | 1.3 | 1.1 |
| 2021 | 13.58 | 21.5–20.7 | 21.42 | 18.0–25.4 | 24.68 | 20.1 30.2 | 1.6 | 1.8 |
| 2023 | >30 | | >30 | | >30 | | | |
| 2026 | 25.38 | 21.1–30.5 | 26.67 | 23.2–30.7 | 37.64 | 21.8–65.1 | 1.1 | 1.5 |

Figure 1:
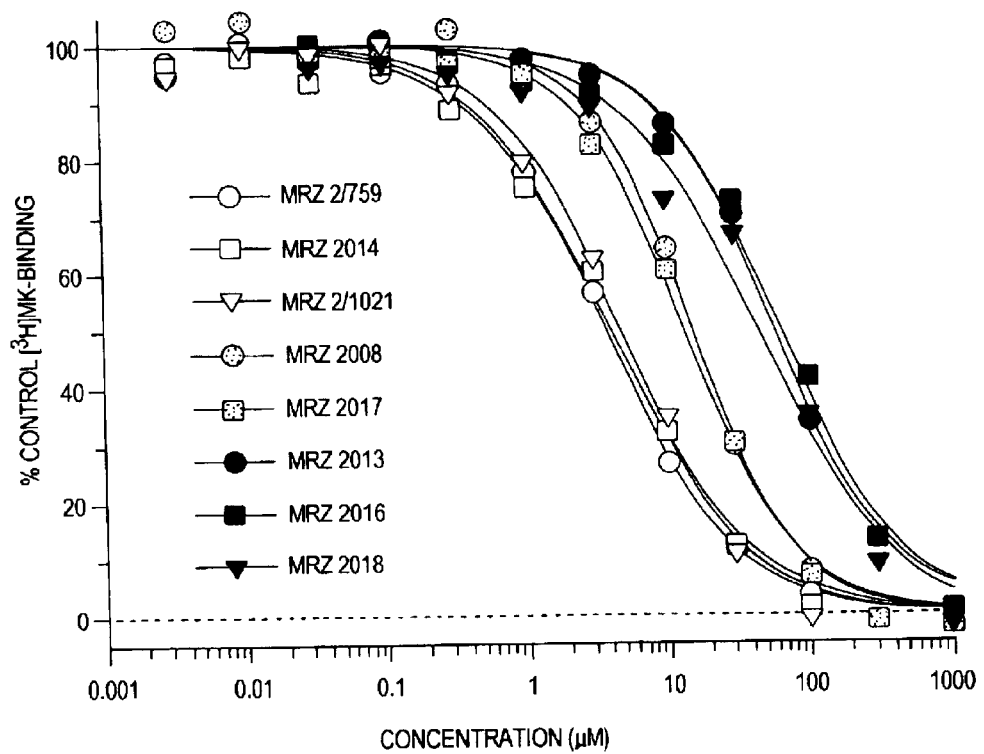
FIG. 1 shows the values obtained for representative compounds of the invention in the specific [$^3$H]-MK-801 binding test plotted against concentration.
Figures 2A, 2B:
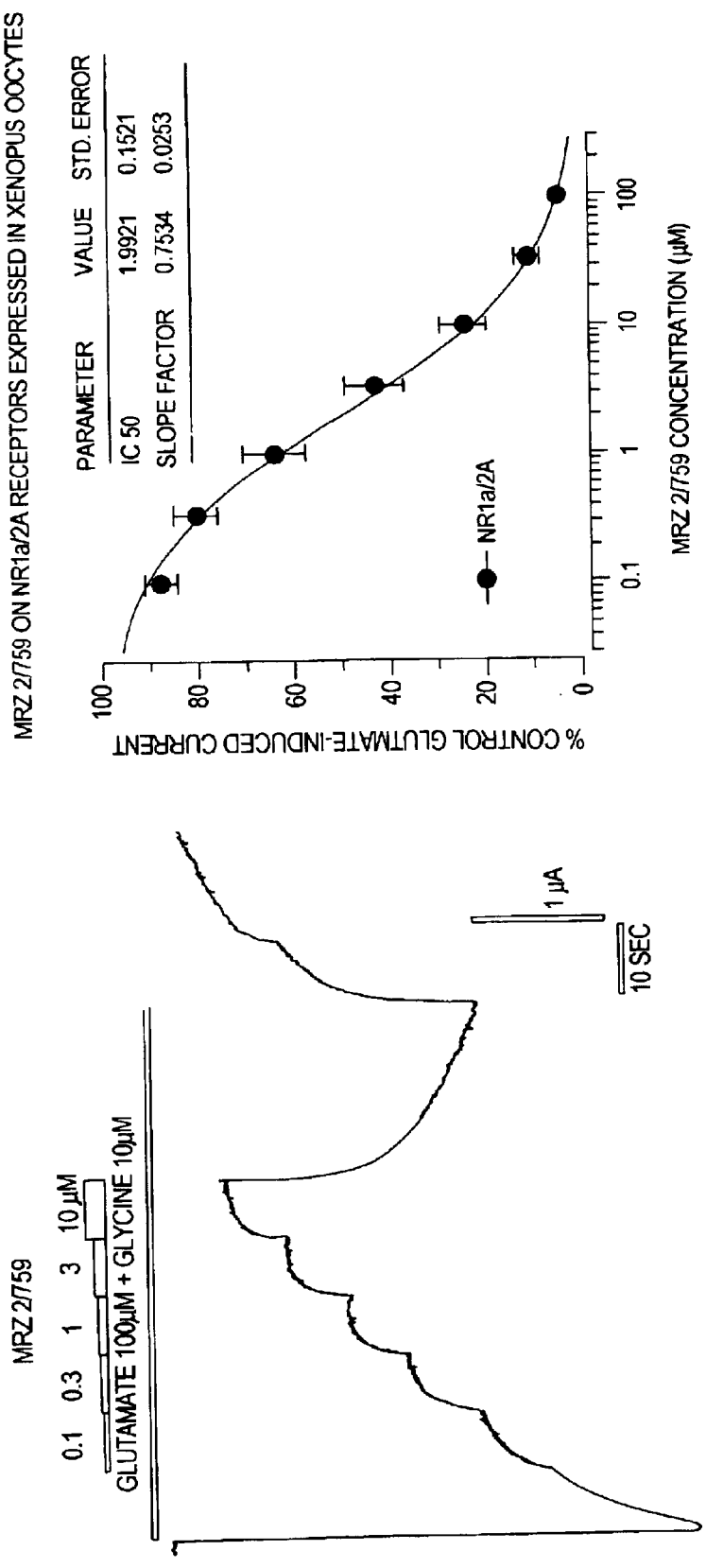
FIG. 2A and FIG. 2B show the effect of MRZ 2/759 on NMDA receptors expressed in *Xenopus oocytes*.
Figure 3:
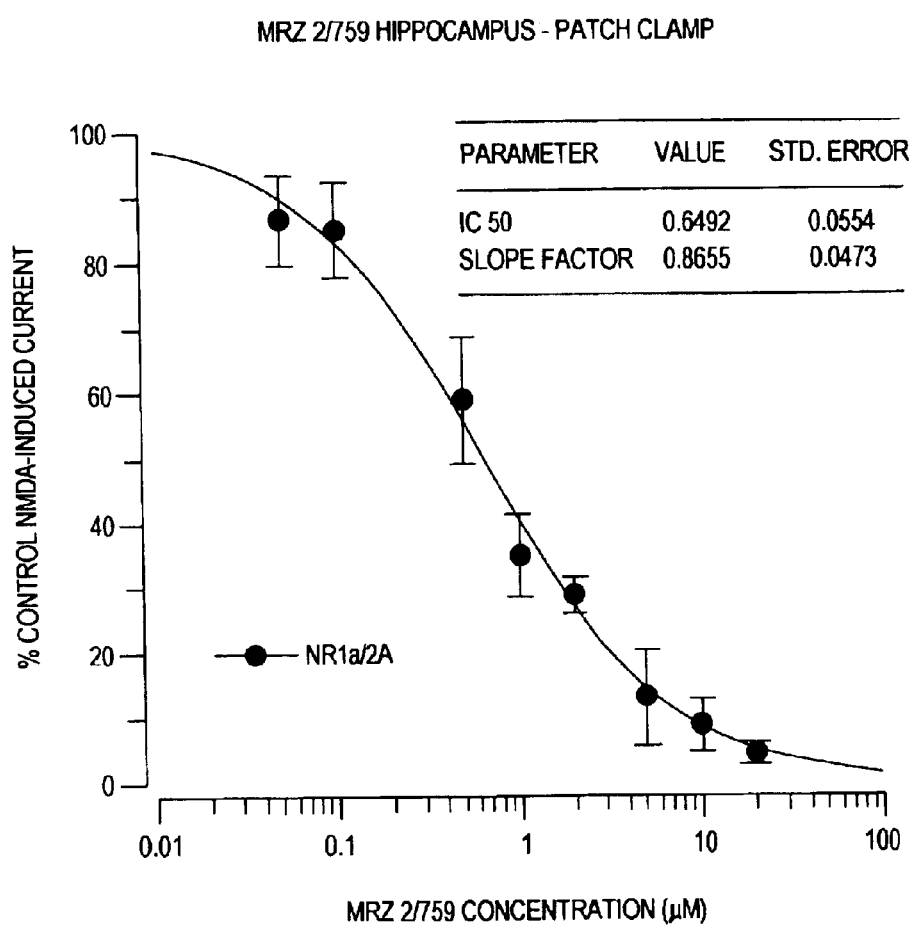
FIG. 3 shows the effect of MRZ 2/759 on NMDA-induced currents in patch-clamp experiments.

In conclusion, from the foregoing, it is apparent that the present invention provides novel, valuable, and unexpected applications and uses of the compounds of the present invention, which compounds comprise the active principle especially a human. 1. Excitotoxicity such as ischaemia during stroke, trauma, hypoxia, hypoglycemia, glaucoma, and hepatic encephalopathy. 2. Chronic neurodegenerative diseases such as Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, Creutzfeldt-Jakob disease. 3. Other disorders related to long term plastic changes in the central nervous system selected from chronic pain, drug tolerance, dependence and addiction (e.g., opioids, cocaine, benzodiazepines, nicotine, and alcohol). 4.

Epilepsy, tardive dyskinesia, schizophrenia, anxiety, depression, acute pain, spasticity, and tinnitus.

Furthermore, it was found that these compounds are neuronal nicotinic receptor and $5HT_3$ receptor antagonists as well. The compounds of the invention thus find application in the treatment of disorders in a living animal body, especially a human, in both nicotinic and $5HT_3$ receptor mediated indications for both symptomatic and neuroprotective purposes (e.g. emesis, nicotine abuse, schizophrenia, cerebellar tremor, IBS, migraine, depressive disorders, cognitive disorders, Parkinson's disease treatment-related psychosis and appetite disorders).

In addition, as already stated, due to at least in part to their amine substituent, the compounds of the present invention are also effective in indications not related to the aforementioned mechanism of action, exhibiting immunomodulatory activity, antimalaria and antitrypanozomal potency, anti-Borna virus, anti-HSV and anti-Hepatitis C virus activity.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the compounds of the present invention in the manufacture of a medicament for the treatment of a living animal for inhibition of progression or alleviation of selected ailments or conditions, particularly ailments or conditions susceptible to treatment with an NMDA receptor antagonist, neuronal nicotinic receptor antagonist, $5HT_3$ antagonist, or a compound exhibiting immunomodulatory activity, antimalaria and antitrypanosomal potency, anti-Borna virus, and anti-HSV and anti-Hepatitis C virus activity, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing.

It is to be understood that the invention is not to be limited to the exact details of operation, or the exact compositions, methods, procedures, or embodiments shown and described, as obvious modifications and equivalents will be apparent to one skilled in the art, and the invention is therefore to be limited only by the full scope which can be legally accorded to the appended claims.

REFERENCES

1. R. L. Frank, H. K. Hall (1950) J. Am. Chem. Soc. 72:1645–1648.
2. G. A. Hiegel, P. Burk. (1973) J. Org. Chem. 38:3637–3639.
3. N. F. Firrell, P. W. Hickmott. (1970) J. Chem. Soc. C:716–719.
4. G. H. Posner, L. L. Frye. (1984) Isr. J. Chem. 24:88–92.
5. G. L. Lemiere, T. A. van Osselaer, F. C. Anderweireldt. (1978) Bull. Soc. Chim. Belg. 87:771–782.
6. H. O. House, J. M. Wilkins. (1976) J. Org. Chem. 41:(25) 4031–4033.
7. A. R. Greenaway, W. B. Whalley. (1976) J. Chem. Soc. P.T. 1. :1385–1389.
8. S. Matsuzawa, Y. Horiguchi, E. Nakamura, I. Kuwajima. (1989) Tetrahedron 45:(2) 349–362.
9. H. O. House, W. F. Fischer. (1968) J. Org. Chem. 33:(3) 949–956.
10. Chiurdoglu, G., Maquestiau, A. (1954) Bull. Soc. Chim. Belg. 63: 357–378.
11. Zaidlewicz, M., Uzarewicz A., Zacharewicz, W. (1964) Roczniki Chem. 38: 591–597.
12. Crossley, A. W., Gilling, C. (1910) J. Chem. Soc. 2218.
13. Zaidlewicz, M., Uzarewicz, A. (1971) Roczniki Chem. 45: 1187–1194.
14. Lutz, E. T., van der Maas, J. H. (1981) Spectrochim. Acta, A. 38A: 283.
15. Lutz, E. T., van der Maas, J. H. (1981) Spectrochim. Acta, A. 37A: 129–134.
16. Ramalingam K., Balasubramanian, M., Baliah, V. (1972) Indian J. Chem. 10: 366–369.
17. Hamlin, K. E., Freifelder, M. (1953) J. Am. Chem. Soc. 75: 369–373.
18. Hassner, A., Fibinger, R., Andisik, D. (1984) J. Org. Chem. 49: 4237–4244.
19. W. Danysz, C. G. Parsons, I. Bresink, G. Quack (1995) Drug News Perspect. 8:261–277.
20. J. D. Leander, R. R. Lawson, P. L., Ornstein, D. M. Zimmerman (1988) Brain Res. 448:115–120.
21. C. G. Parsons, G. Quack, I. Bresink, L. Baran, E. Przegalinski, W. Kostowski, P. Krzascik, S. Hartmann, W. Danysz (1995). Neuropharmacology 34:1239–1258.
22. M. A. Rogawski (1993) Trends Pharmacol. Sci. 14:325–331.
23. Booher J. and Sensenbrenner M. (1972). Neurobiology 2:97–105.
24. Dichter, M. (1987) Brain Research 149:279.

We claim:

1. A compound selected from those of formula I:

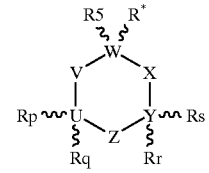

wherein:

R* is —(A)$_n$—(A)$_n$—(CR$^1$R$^2$)$_m$—NR$^3$R$^4$, n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), R$^1$ and R$^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), R$^3$ and R$^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloallcene, including substituted (alkyl ($C_1$–$C_6$), substituted alkenyl ($C_2$–$C_6$)) 3–7-membered azacycloalkafle or azacycloalkene, $R^5$ is independently selected from the group consisting of linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group $R^*$ to form a double bond, or $R^5$ combine with the carbon atom of W to which it is attached and an adjacent ring carbon atom to form a double bond, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, provided that U—V—W—X—Y—Z is selected from
cyclohexane,
cyclohex-2-ene,
cyclohex-3-ene,
cyclohex-1,4-diene,
cyclohex-1,5-diene,
cyclohex-2,4-diene, and
cyclohex-2,5-diene, and provided that at least one of $R_p$ and $R_q$, are not hydrogen and at least one of $R_r$, and $R^s$ are not hydrogen, and provided that when U-Z equals cyclohexane, then at least one of —(A)$_n$—(CR$^1$R$^2$)$_{m,R}{^3}$, R$^4$, R$^5$, R$_p$, R$_q$, R$_r$, and R$^s$ is linear or branched lower alkenyl ($C_2$–$C_6$) or linear or branched lower alkynyl ($C_2$–$C_6$), and its optical isomers and pharmaceutically-acceptable acid or base addition salt thereof.

2. A method-of-treating a living animal for alleviation of a condition treatable by a NMDA antagonist comprising the step of administering to the living animal an amount of a compound selected from those of formula I:

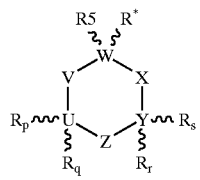

wherein:
R* is —(A)$_n$—(CR$^1$R$^2$)$_m$—NR$^3$R$^4$,
n+m=0, 1, or 2,
A is selected from the group consisting of linear or branched lower alkyl ($C_1$–$C_6$), linear or branched lower alkenyl ($C_2$–$C_6$), and linear or branched lower alkynyl ($C_2$–$C_6$),
$R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$),
$R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group $R^*$ to form a double bond, or $R^5$ combine with the carbon atom of W to which it is attached and an adjacent ring carbon atom to form a double bond, or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U—Z equals cyclohexane, then at least one of —(A)$_n$—(CR$^1$R$^2$)$_m$—, R$^3$, R$^4$, R$^5$, R$_p$, R$_q$, R$_r$ is linear or branched lower alkenyl ($C_2$–$C_6$) or linear or branched lower alkynyl (($C_{22}$–$C_6$), its optical isomers and pharmaceutically-acceptable acid or base addition salts thereof, which is effective for alleviation of said condition.

3. A method-of-treating a living animal for alleviation of a condition treatable by a compound selected for its immunomodulatory, anti-malarial, anti-Borna virus, or anti-Hepatitis C, anti-trypanosomal, and anti-HSV efficacy, comprising the step of administering to the living animal an amount of a compound selected from those of formula I:

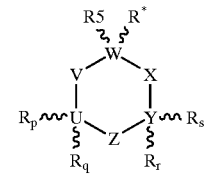

wherein:
R* is —(A)$_n$—(CR$^1$R$^2$)$_m$—NR$^3$R$^4$,
n+m=0, 1, or 2,
A is selected from the group consisting of linear or branched lower alkyl ($C_1$–$C_6$), linear or branched lower alkenyl ($C_2$–$C_6$), and linear or branched lower alkynyl ($C_2$–$C_6$),
$R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$),
$R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group $R^*$ to form a double bond, or $R^5$ may combine with the carbon atom of W to which it is attached and an adjacent ring carbon atom to form a double bond or $R_p$, $R_q$, $R^r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U—V—W—X—Y—Z is selected from:
  cyclohexane,
  cyclohex-1-ene,
  cyclohex-2-ene,
  cyclohex-3-ene,
  cyclohex-1,3-diene,
  cyclohex-1,4-diene,
  cyclohex-1,5-diene,
  cyclohex-2,4-diene, and
  cyclohex-2,5-diene, and provided that when U—Z equals cyclohexane, then at least one of —(A)$_n$—(CR$^1$R$^2$)$_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition.

4. A method-of-treating a living animal for alleviation of a condition treatable by an NMDA antagonist selected from the group consisting of excitotoxicity selected from ischaemia during stroke, trauma, hypoxia, hypoglycemia, glaucoma, and hepatic encephalopathy, chronic neurodegenerative diseases selected from Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, and Creutzfeldt-Jakob disease, other disorders related to long term plastic changes in the central nervous system selected from chronic pain, drug tolerance, dependence and addiction (e.g., opioids, cocaine, benzodiazepines, nicotine, and alcohol), and epilepsy, tardive dyskinesia, L-DOPA-induced dyskinesia, schizophrenia, anxiety, depression, acute pain, spasticity, and tinnitus, comprising the step of administering to the living animal an amount of a compound selected from those of formula I:

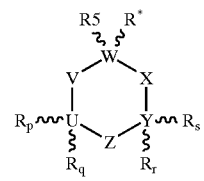

wherein:
  $R^*$ is —(A)$_n$—(CR$^1$R$^2$)$_m$—NR$^3$R$^4$,
  n+m=0, 1, or 2,
  A is selected from the group consisting of linear or branched lower alkyl ($C_1$–$C_6$), linear or branched lower alkenyl ($C_2$–$C_6$), and linear or branched lower alkynyl ($C_2$–$C_6$),
  $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$),
  $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene,
  $R^5$, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R^5$ may combine with the carbon atom of W to which it is attached and an adjacent carbon atom of the group $R^*$ to form a double bond, or $R^5$ may combine with the carbon atom of W to which it is attached and an adjacent ring carbon atom to form a double bond, $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, and provided that U-V-W-X-Y-Z is selected from:
  cyclohexane,
  cyclohex-1-ene,
  cyclohex-2-ene.
  cyclohex-3-ene,
  cyclohex-1,3-diene,
  cyclohex-1,4-diene,
  cyclohex-1,5-diene,
  cyclohex-2,4-diene, and
  cyclohex-2,5-diene, and provided that when U—Z equals cyclohexane, then at least one of —(A)$_n$—(CR$^1$R$^2$)$_m$—, $R^3$, $R^4$, $R^5$, $R_p$, $R_q$, $R_r$ is linear or branched lower alkenyl ($C_2$–$C_6$) or linear or branched lower alkynyl ($C_2$–$C_6$), its optical isomers and pharmaceutically-acceptable acid or base addition salts thereof, which is effective for alleviation of said condition.

5. A method-of-treating a living animal for alleviation of a condition treatable by a 5HT$_3$ receptor antagonist, comprising the step of administering to the living animal an amount of a compound selected from those of formula I:

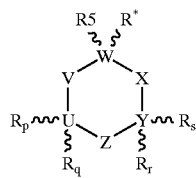

wherein:

R is —(A)$_n$—(CR$^1$R$^2$)$_m$—NR$^3$R$^4$, n+m=0, 1, or 2,

A is selected from the group consisting of linear or branched lower alkyl (C$_1$–C$_6$), linear or branched lower alkenyl (C$_2$–C$_6$), and linear or branched lower alkynyl (C$_2$–C$_6$), R$^1$ and R$^2$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), R$^3$ and R$^4$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or together form alkylene (C$_2$–C$_{10}$) or alkenylene (C$_2$–C$_{10}$) or together with the N form a 3–7-membered azacycloalkane or azacycloalkene, including substituted (alkyl (C$_1$–C$_6$), substituted alkenyl (C$_2$–C$_6$)) 3–7-membered azacycloalkane or azacycloalkene, R$^5$, R$^p$, R$_q$, R$_r$, and R$_s$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or R$^5$ may combine with the carbon atom of W to which it is attached and an adjacent carbon atom of the group R* to form a double bond, or R$^5$ may combine with the carbon atom of W to which it is attached and an adjacent ring carbon atom to form a double bond, R$_p$, R$^q$, R$_r$, and R$_s$ independently may combine with the carbon to which it is attached and the next adjacent carbon to form a double bond, or R$_p$, R$_q$, R$_r$, and R$_s$ independently may form a double bond with U or with Y to which it is attached, and provided that U—V—W—X—Y—Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U—Z equals cyclohexane, then at least one —(A)$_n$—(CR$^1$R$^2$)$_m$—, R$^3$, R$^4$, R$^5$, R$_p$, R$_q$, R$_r$ is linear or branched lower alkenyl (C$_2$–C$_6$) or linear or branched lower alkynyl (C$_2$–C$_6$), its optical isomers and pharmaceutically-acceptable acid or base addition salts thereof, which is effective for alleviation of said condition.

6. A method-of-treating a living animal for alleviation of a condition treatable by a neuronal nicotinic receptor antagonist, comprising the step of administering to the living animal an amount of a compound selected from those of formula I:

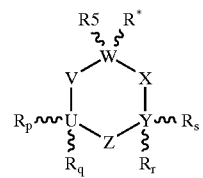

wherein:

R* is —(A)$_n$—(CR$^1$R$^2$)$_m$—NR$^3$R$^4$, n+m=0, 1, or 2,

A is selected from the group consisting of linear or branched lower alkyl (C$_1$–C$_6$), linear or branched lower alkenyl (C$_2$–C$_6$), and linear or branched lower alkynyl (C$_2$–C$_6$), R$^1$ and R$^2$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), R$^3$ and R$^4$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or together form alkylene (C$_2$–C$_{10}$) or alkenylene (C$_2$–C$_{10}$) or together with the N form a 3–7-membered azacycloalkane or azacycloalkene, including substituted (alkyl (C$_1$–C$_6$), substituted alkenyl (C$_2$–C$_6$)) 3–7-membered azacycloallcane or azacycloalkene, R$^5$, R$_p$, R$_q$, R$_r$, and R$_s$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or R$^5$ may combine with the carbon atom of W to which it is attached and an adjacent carbon atom of the group R* to form a double bond, or R$^5$ may combine with the carbon atom of W to which it is attached and an adjacent ring carbon atom to form a double bond, R$_p$, R$_q$, R$_r$, and R$_s$ independently may combine with the carbon to which it is attached and the next adjacent carbon to form a double bond, or R$_p$, R$_q$, R$_r$, and R$_s$ independently may form a double bond with U or with Y to which it is attached, and provided that U—V—W—X—Y—Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene, and provided that when U—Z equals cyclohexane, then at least one of —(A)$_n$—(CR$^1$R$^2$)$_m$—, R$^3$, R$^4$, R$^5$, R$_p$, R$_q$, R$_r$ is linear or branched lower alkenyl (C$_2$–C$_6$) or linear or branched lower alkynyl (C$_2$–C$_6$), its optical isomers and pharmaceutically-acceptable acid or base addition salts thereof, which is effective for alleviation of said condition.

7. A method-of-treating a living animal for alleviation of a condition treatable by a 5HT$_3$ antagonist selected from the group consisting of anxiety disorders, depressive disorders, Schizophrenia and treatment related psychosis, drug and alcohol abuse disorders, cognitive disorders, Alzheimer's disease, Parkinson's disease, cerebellar tremor, migraine, appetite disorders, inflammatory bowel syndrome (IBS), and eniesis, comprising the step of administering to the living animal an amount of a compound selected from those of formula I:

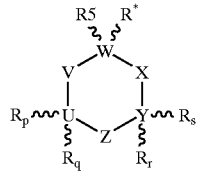

wherein:
R* is —(A)$_n$—(CR$^1$R$^2$)$_m$—NR$^3$R$^4$,
n+m=0, 1, or 2,
A is selected from the group consisting of linear or branched lower alkyl (C$_1$–C$_6$), linear or branched lower alkenyl (C$_2$–C$_6$), and linear or branched lower alkynyl (C$_2$–C$_6$),
R$^1$ and R$^2$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$),
R$^3$ and R$^4$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or together form alkylene (C$_2$–C$_{10}$) or alkenylene (C$_2$–C$_{10}$) or together with the N form a 3–7-membered azacycloalkane or azacycloalkene, including substituted (alkyl (C$_1$–C$_6$), substituted alkenyl (C$_2$–C$_6$)) 3–7-membered azacycloalkane or azacycloalkene,
R$^5$, R$_p$, R$_q$, R$_r$, and R$_s$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or R$^5$ may combine with the carbon atom of W to which it is attached and an adjacent carbon atom of the group R* to form a double bond, or R$^5$ may combine with the carbon atom of W to which it is attached and an adjacent ring carbon atom to form a double bond, or R$_p$, R$_q$, R$_r$, and R$_s$ independently may combine with the carbon to which it is attached and the next adjacent carbon to form a double bond, or R$_p$, R$_q$, R$_r$, and R$_s$ independently may form a double bond with U or with Y to which it is attached, and
provided that U—V—W—X—Y—Z is selected from:
cyclohexane,
cyclohex-1-ene,
cyclohex-2-ene,
cyclohex-3-one,
cyclohex-1,3-diene,
cyclohex-1,4-diene,
cyclohex-1,5-diene,
cyclohex-2,4-diene, and
cyclohex-2,5-diene,
and provided that when U—Z equals cyclohexane, then at least one of —(A)$_n$—(CR$^1$R$^2$)$_m$—, R$^3$, R$^4$, R$^5$, R$_p$, R$_q$, R$_r$ is linear or branched lower alkenyl (C$_2$–C$_6$) or linear or branched lower alkynyl (C$_2$–C$_6$),
its optical isomers and pharmaceutically-acceptable acid or base addition salts thereof, which is effective for alleviation of said condition.

8. A method-of-treating a living animal for alleviation of a condition treatable by a neuronal nicotinic receptor antagonist selected from the group consisting of Tourette's syndrome, anxiety disorders, Schizophrenia, drug abuse, nicotine abuse, cocaine abuse, dyskinesia (Morbus Huntington, L-DOPA-induced), attention deficit hyperactivity disorder (ADHD), Alzheimer's disease, Parkinson's disease, and pain, comprising the step of administering to the living animal an amount of a compound selected from those of formula I:

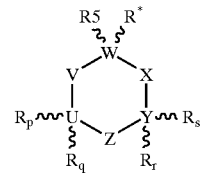

wherein:
R is —(A)$_n$—(CR$^1$R$^2$)$_m$—NR$^3$R$^4$,
n+m=0, 1, or 2,
A is selected from the group consisting of linear or branched lower alkyl (C$_1$–C$_6$), linear or branched lower alkenyl (C$_2$–C$_6$), and linear or branched lower alkynyl (C$_2$–C$_6$),
R$^1$ and R$^2$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$),
R$^3$ and R$^4$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or together form alkylene (C$_2$–C$_{10}$) or alkenylene (C$_2$–C$_{10}$) or together with the N form a 3–7-membered azacycloalkane or azacycloalkene, including substituted (alkyl (C$_1$–C$_6$), substituted alkenyl (C$_2$–C$_6$)) 3–7-membered azacycloalkane or azacycloalkene,
R$^5$, R$_p$, R$_q$, R$_r$, and R$_s$ are independently selected from the group consisting of hydrogen, linear or branched lower alkyl (C$_1$–C$_6$), linear or branched lower alkenyl (C$_2$–C$_6$), and linear or branched lower alkynyl (C$_2$–C$_6$), or R$^5$ may combine with the carbon atom of W to which it is attached and an adjacent carbon atom of the group R* to form a double bond, or R$^5$ may combine with the carbon atom of W to which it is attached and an adjacent ring carbon atom to form a double bond, or R$^p$, R$_q$, R$_r$, and R$_s$ independently may combine with the carbon to which it is attached and the next adjacent carbon to form a double bond, or R$_p$, R$_q$, R$_r$, and R$_s$ independently may form a double bond with U or with Y to which it is attached, and
provided that U—V—W—X—Y—Z is selected from:
cyclohexane,
cyclohex-1-ene,
cyclohex-2-ene,
cyclohex-3-ene,
cyclohex-1,3-diene,
cyclohex-1,4-diene,
cyclohex-1,5-diene,
cyclohex-2,4-diene, and
cyclohex-2,5-diene,
and provided that when U—Z equals cyclohexane, then at least one of —(A)$_n$—(CR$^1$R$^2$)$_m$—, R$^3$, R$^4$, R$^5$, R$_p$, R$_q$, R$_r$ is linear or branched lower alkenyl (C$_2$–C$_6$) or linear or branched lower alkynyl (C$_2$–C$_6$),
its optical isomers and pharmaceutically-acceptable acid or base addition salts thereof, which is effective for alleviation of said condition.

9. A pharmaceutical composition having a compound selected from those of formula I:

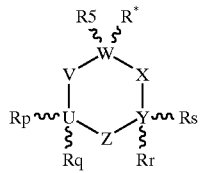

wherein:

$R^*$ is —$(A)_n$—$(CR^1R^2)_m$—$NR^3R^4$, n+m=0, 1, or 2,

A is selected from the group consisting of linear or branched lower alkyl ($C_1$–$C_6$), linear or branched lower alkenyl ($C_2$–$C_6$), and linear or branched lower alkynyl ($C_2$–$C_6$), $R^1$ and $R^2$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), $R^3$ and $R^4$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or together form alkylene ($C_2$–$C_{10}$) or alkenylene ($C_2$–$C_{10}$) or together with the N form a 3–7-membered azacycloalkane or azacycloalkene, including substituted (alkyl ($C_1$–$C_6$), substituted alkenyl ($C_2$–$C_6$)) 3–7-membered azacycloalkane or azacycloalkene, $R^5$ is independently selected from the group consisting of linear or branched lower alkyl ($C_1$–$C_6$), linear or branched lower alkenyl ($C_2$–$C_6$), and linear or branched lower alkynyl ($C_2$–$C_6$), or $^5$ may combine with the carbon atom of W to which it is attached and an adjacent carbon atom of the group $R^*$ to form a double bond, or $R^5$ may combine with the carbon atom of W to which it is attached and an adjacent ring carbon atom to form a double bond, $R_p$, $R_q$, $R_r$, and $R_s$ are independently selected from the group consisting of hydrogen, linear or branched lower alkyl ($C_1$–$C_6$), linear or branched lower alkenyl ($C_2$–$C_6$), and linear or branched lower alkynyl ($C_2$–$C_6$), or $R_p$, $R_q$, $R_r$, and $R_s$ independently may combine with the carbon to which it is attached and the next adjacent carbon to form a double bond, or $R_p$, $R_q$, $R_r$, and $R_s$ independently may form a double bond with U or with Y to which it is attached, provided that U—V—W—X—Y—Z is selected from
cyclohexane,
cyclohex-2-ene,
cyclohex-3-ene,
cyclohex-1,4-diene,
cyclohex-1,5-diene,
cyclohex-2,4-diene, and
cyclohex-2,5-diene, and provided that at least one of $R_p$, and $R_q$, are not hydrogen and at least one of $R_r$, and $R_s$ are not hydrogen, and provided that when U—Z equals cyclohexane, then at least one of —$(A)_n$—$(CR^1R^2)_m$—, $R^3$, $R^4$, $R^5$, $R_p$, $R_q$, $R_r$, and $R_s$ is linear or branched lower alkenyl ($C_2$–$C_6$) or linear or branched lower alkynyl ($C_2$–$C_6$), and provided that when U—Z equals cyclohexane, then $R^5$ cannot be hydrogen, in combination with one or more pharmaceutically-acceptable diluents, excipients, or carriers.

* * * * *

UNITED STATES PATENT AND TRADEMARK OFFICE
CERTIFICATE OF CORRECTION

PATENT NO.  : 6,828,462 B2
DATED       : December 7, 2004
INVENTOR(S) : Markus Henrich et al.

It is certified that error appears in the above-identified patent and that said Letters Patent is hereby corrected as shown below:

Column 42,
Line 48, "-$(A)_n$--$(A)_n$-" should be -- --$(A)_n$- --.
Lines 65 and 67, "azacycloalkafle" should be -- azacycloalkane --.

Column 43,
Line 32, "$_{m,R}{}^3$" should be -- $_m$-, $R^3$ --.

Column 44,
Line 32, "(($C_{22}$-$C_6$)" should be -- ($C_2$-$C_6$) --.

Column 45,
Line 15, "$R^r$" should be -- $R_r$ --.
Line 45, "iscbaemia" should be -- ischaemia --.

Column 46,
Lines 28-29, "azacycloallcane" should be -- azacycloalkane --.
Line 40, "bond, $R_p$ ," should be -- bond, or $R_p$ , --.

Column 47,
Line 11, "R is" should be -- R* is --.
Line 39, "bond, $R_p$ ," should be -- bond, or $R_p$ , --.
Line 57, "least one" should be -- least one of --.

Column 48,
Line 29, "azacycloallcane" should be -- azacycloalkane --.
Line 38, "bond, $R_p$ ," should be -- bond, or $R_p$ , --.

Column 49,
Line 2, "eniesis" should be -- emesis --.

Column 50,
Line 19, "R is" should be -- R* is --.

UNITED STATES PATENT AND TRADEMARK OFFICE
CERTIFICATE OF CORRECTION

PATENT NO. : 6,828,462 B2
DATED : December 7, 2004
INVENTOR(S) : Markus Henrich et al.

It is certified that error appears in the above-identified patent and that said Letters Patent is hereby corrected as shown below:

Column 51,
Line 35, "or $^5$" should be -- or $R^5$ --.

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,828,462 B2
DATED : December 7, 2004
INVENTOR(S) : Markus Henrich et al.

It is certified that error appears in the above-identified patent and that said Letters Patent is hereby corrected as shown below:

Column 42,
Line 48, "-$(A)_n$--$(A)_n$-" should be -- --$(A)_n$- --.
Line 65, "azacycloallcene" should be -- azacycloalkene --.
Line 67, "azacycloalkafle" should be -- azacycloalkane --.

Column 43,
Line 32, "$_{m,R}{}^3$" should be -- $_m$-, $R^3$ --.

Column 44,
Line 32, "($(C_{22}-C_6)$" should be -- $(C_2-C_6)$ --.

Column 45,
Line 15, "$R^r$" should be -- $R_r$ --.
Line 45, "iscbaemia" should be -- ischaemia --.

Column 46,
Lines 28-29, "azacycloallcane" should be -- azacycloalkane --.
Line 40, "bond, $R_p$ ," should be -- bond, or $R_p$ , --.

Column 47,
Line 11, "R is" should be -- R* is --.
Line 39, "bond, $R_p$ ," should be -- bond, or $R_p$ , --.
Line 57, "least one" should be -- least one of --.

Column 48,
Line 29, "azacycloallcane" should be -- azacycloalkane --.
Line 38, "bond, $R_p$ ," should be -- bond, or $R_p$ , --.

Column 49,
Line 2, "eniesis" should be -- emesis --.

Column 50,
Line 19, "R is" should be -- R* is --.

UNITED STATES PATENT AND TRADEMARK OFFICE
CERTIFICATE OF CORRECTION

PATENT NO.    : 6,828,462 B2
DATED         : December 7, 2004
INVENTOR(S)   : Markus Henrich et al.

It is certified that error appears in the above-identified patent and that said Letters Patent is hereby corrected as shown below:

Column 51,
Line 35, "or $^5$" should be -- or $R^5$ --.

This certificate supersedes the Certificate of Correction issued April 19, 2005.

Signed and Sealed this

Eleventh Day of March, 2008

JON W. DUDAS
*Director of the United States Patent and Trademark Office*